US012576280B1

(12) United States Patent
Villamil et al.

(10) Patent No.: US 12,576,280 B1
(45) Date of Patent: Mar. 17, 2026

(54) ACTIVE MEDICAL DEVICE HAVING A TERMINAL HOUSING ASSEMBLY CONNECTED TO A PRINTED CIRCUIT BOARD ASSEMBLY WITHOUT AN INTERMEDIATE FEEDTHROUGH

(71) Applicant: Greatbatch Ltd., Clarence, NY (US)

(72) Inventors: Luis Daniel Villamil, Montevideo (UY); Camila Duarte, Montevideo (UY); Ignacio Agustin Armesto, Montevideo (UY)

(73) Assignee: Greatbatch Ltd., Clarence, NY (US)

( * ) Notice: Subject to any disclaimer, the term of this patent is extended or adjusted under 35 U.S.C. 154(b) by 211 days.

(21) Appl. No.: 18/411,703

(22) Filed: Jan. 12, 2024

Related U.S. Application Data

(60) Provisional application No. 63/438,816, filed on Jan. 13, 2023.

(51) Int. Cl.
*A61N 1/375* (2006.01)
*A61B 5/00* (2006.01)
*H01R 12/57* (2011.01)

(52) U.S. Cl.
CPC ............ *A61N 1/3758* (2013.01); *A61B 5/686* (2013.01); *A61N 1/3752* (2013.01); *H01R 12/57* (2013.01)

(58) Field of Classification Search
CPC ..... A61N 1/375; A61N 1/3752; A61N 1/3758
See application file for complete search history.

(56) References Cited

U.S. PATENT DOCUMENTS

| | | | |
|---|---|---|---|
| 8,131,370 B2 | 3/2012 | Janzig et al. | |
| 10,363,424 B2 | 7/2019 | Janzig et al. | |
| 11,213,673 B2 | 1/2022 | Janzig et al. | |
| 11,559,694 B2 | 1/2023 | Janzig et al. | |
| 2009/0112272 A1* | 4/2009 | Schleicher | A61N 1/37235 |
| | | | 607/116 |
| 2014/0243942 A1* | 8/2014 | Kast | A61N 1/3752 |
| | | | 29/878 |
| 2015/0094789 A1* | 4/2015 | Janzig | A61N 1/3752 |
| | | | 607/116 |
| 2021/0186422 A1 | 6/2021 | Nielsen et al. | |
| 2021/0187306 A1* | 6/2021 | Spadgenske | A61N 1/3752 |
| 2022/0008734 A1* | 1/2022 | English | A61N 1/3752 |

* cited by examiner

*Primary Examiner* — Michael W Kahelin
(74) *Attorney, Agent, or Firm* — Michael F Scalise

(57) ABSTRACT

An AMD has a main housing closed by an end cap. A PCB supports electrical contacts connected to electronic components. An electrical power source powers the electronic components. A metallic sleeve connected to an inner surface of the end cap has a sleeve lumen aligned with a cap lead opening. A terminal housing assembly has a number of insulator rings connected to a number of the metallic terminal housings in an alternating sequence extending distally from the sleeve. The insulator rings support silicone ring seals and the terminal housings support canted coil springs. Jumper wires connect the terminal housings of the terminal housing assembly to the electrical contacts of the PCB without an intermediate feedthrough. In use, the electrical contacts of a lead are moved through the sleeve lumen and into the terminal housing assembly to connect the electrical contacts to the canted coil springs of the terminal housings.

23 Claims, 12 Drawing Sheets

1

ACTIVE MEDICAL DEVICE HAVING A TERMINAL HOUSING ASSEMBLY CONNECTED TO A PRINTED CIRCUIT BOARD ASSEMBLY WITHOUT AN INTERMEDIATE FEEDTHROUGH

CROSS-REFERENCE TO RELATED APPLICATION

This application claims priority to U.S. Provisional Application Ser. No. 63/438,816, filed on Jan. 13, 2023.

BACKGROUND OF THE INVENTION

1. Field of the Invention

The present invention relates to the field of implantable medical devices. More particularly, the present invention relates to a miniature-sized active medical device (AMD) that is designed to deliver electrical stimulation to a patient or sense biological signals from body tissue. A miniature-sized AMD is defined as a medical device that has a volume of less than about 3 cc. The AMD can be implanted in a patient's body or worn externally on the body.

The desire to make AMDs as small as possible is an active area of innovation. Implanting a miniature-sized AMD is advantageous over implanting a conventionally-sized pulse generator for many reasons. Chief among them is that the implantation procedure can be performed with far less surgical trauma to the patient. As long as the miniature AMD has the same or similar functionality as an AMD of a conventional size, subjecting the patient to less trauma represents an advancement in the industry. This includes implanting a miniature-sized neurostimulator for pain therapy. Additionally, a miniature-sized neurostimulator can be applied to many more nerves, particularly to smaller nerves, than a relatively larger conventionally-sized neurostimulator. Further, an externally worn miniature AMD would be expected to be less bothersome to a patient than a larger version of the same device.

2. Prior Art

A conventional active medical device has a header assembly that is detachably connected to a lead provided with at least two spaced-apart distal electrodes. The electrodes, which are configured to send electrical pulses to the surrounding body tissue or sense biological signals from the tissue, are assembled into the distal end of the lead to contact the surrounding tissue while the proximal lead end is received in the header assembly of the medical device. The device header has a number of terminal housings that are configured to electrically connect to the lead. Typical AMD configurations have a plurality of terminal housings aligned in-line or as a co-axial system with an insulator positioned between adjacent housings. However, there are size limitations regarding how small the industry can miniaturize such in-line lead attachment configurations using current design technology.

Other efforts to miniaturize AMDs are focused on integrating the active medical device with the lead into a single device. Although this simplifies the connection between the medical device and its pacing/sensing lead, such medical devices cannot be customized according to the physical characteristics of the implantation procedure or the patient's medical condition.

Therefore, there is an ongoing need for an AMD, whether implantable or intended to be worn externally, that is detachably connectable to a lead to provide both stimulation and sensing capability where there is a high density of electrical contact housings or terminals for connecting a stimulation or sensing lead to the medical device, but in a device having a volume that is less than about 3 cc. A smaller medical device is easier to implant in a patient and would be expected to cause less trauma to the patient. A smaller medical device is also expected to be less bothersome to a patient.

SUMMARY OF THE INVENTION

In a general sense, the present invention relates to an active medical device (AMD) having a device housing comprising a main housing closed by an end cap. The main housing has a housing sidewall extending to a main housing annular edge surrounding a housing opening leading into an interior of the main housing. The end cap comprises a cap sidewall extending to a cap annular edge surrounding a cap main opening leading into an interior of the end cap. The cap annular edge is aligned along an imaginary plane. An end cap lead opening in the cap sidewall defines a lead opening axis that extends through the interior of the end cap to intersect the imaginary plane, and a lateral opening in the cap sidewall defines a lateral opening axis that intersects the lead opening axis. The cap annular edge is connected to the main housing annular edge to provide the device housing.

A printed circuit board (PCB) is housed inside the device housing. The PCB supports an x number of electrical contacts connected to a respective one of a y number of electronic components with x and y being at least 2.

An electrical power source housed inside the device housing powers the electronic components.

A metallic sleeve has a sleeve lumen extending along a sleeve axis from a proximal sleeve end to a distal sleeve end. The proximal sleeve end is connected to an inner surface of the end cap at the cap lead opening so that the sleeve lumen is aligned with the lead opening axis of the end cap. The sleeve also has a sleeve lateral opening that intersects the sleeve lumen.

A terminal housing assembly has an m number of insulator rings connected to an n number of terminal housings in an alternating sequence extending distally from the distal sleeve end. In that respect, a first one of the m insulator rings is connected to the distal sleeve end and to a first one of the n terminal housings connected to a second one of the m insulator rings connected to a second one of the n terminal housings. The number of m insulator rings and n terminal housings is the same and ranges from 2 to 24. A terminal plate is connected to a distal-most one of the terminal housings opposite an insulator ring to thereby provide the terminal housing assembly extending outwardly beyond the imaginary plane at the cap annular edge and having a central lumen extending along a central axis aligned with the sleeve and the lead opening axes. Moreover, the insulator rings support respective polymeric ring seals, preferably made of silicone, and the terminal housings support respective metallic annular contact springs, preferably canted coil springs.

An o number of jumper wires directly connect a respective one of the terminal housings to a respective one of the electrical contacts supported on the PCB. Further, the x number of electrical contacts and the o number of jumper wires are the same as the m number of insulator rings and the n number of terminal housings ranging from 2 to 24.

A first portion of the PCB supporting the o number of jumper wires directly connecting a respective one of the n number of terminal housings to a respective one of the x number of electrical contacts resides in the main housing. A second portion of the PCB that does not support the electrical contacts extends into the interior of the end cap. Moreover, the PCB has a PCB edge that extends along a PCB edge axis with the x number of electrical contacts being supported by the PCB at the PCB edge, and the PCB edge axis is parallel to the central axis of the central lumen extending through the terminal housing assembly.

In one embodiment of the present terminal housing assembly, the m number of insulator rings are made of PEEK, and the n number of terminal housings and the sleeve are made of titanium. That way, the terminal housing assembly has the alternating sequence extending distally from the distal sleeve end welded to a first one of the m PEEK insulator rings welded to a first one of the n titanium terminal housings welded to a second one of the m PEEK insulator rings welded to a second one of the n titanium terminal housings, wherein the number of m insulator rings and the n number of terminal housings are the same and they range from 2 to 24. The terminal housing assembly is completed with the terminal plate welded to the distal-most titanium terminal housing.

In another embodiment of the present terminal housing assembly, the m number of insulator rings are made of alumina provided with a titanium metallization, and the n number of terminal housings and the sleeve are made of titanium. That way, the terminal housing assembly has the alternating sequence extending distally from the distal sleeve end welded to a first one of the m titanium metallized alumina insulator rings welded to a first one of the n titanium terminal housings welded to a second one of the m titanium metallized alumina insulator rings welded to a second one of the n titanium terminal housings, wherein the m number of insulator rings and the n number of terminal housings are the same and they range from 2 to 24. The terminal housing assembly is completed with the terminal plate welded to the distal-most titanium terminal housing.

In a further embodiment of the present terminal housing assembly, the distal end of the sleeve has an inwardly-extending annular step. At least a first one of the m number of insulator rings has an outer annular insulator wall with right and left inwardly-extending annular steps, and at least a first one of the n number of terminal housings has an outer annular housing wall with at least a right inwardly-extending annular step. Then, a first ring-shaped braze connects the sleeve annular step to the right annular step of the first one of the m insulator rings, and a second ring-shaped braze connects the left annular step of the first one of the m insulator rings to the right annular step of the first one of the n terminal housings.

In still another embodiment of the present terminal housing assembly, at least the first of the n number of terminal housings has spaced-apart right and left sidewalls extending to an outer annular sidewall, and at least the first and second ones the of m number of insulator rings contact the respective right and left sidewalls of the first of the n terminal housings. Then, a sapphire ring contacts the outer annular sidewall of the first of the n number of terminal housings. The sapphire ring is welded to the first and second of the m insulator rings but not to the first of the n terminal housings.

Continuing, in another embodiment of the present terminal housing assembly, the first of the m number of insulator ring has an outer annular wall with right and left inwardly-extending annular steps at the outer wall. At least the first terminal housing has an outwardly-extending right annular rim that is welded to the left annular step of the first of the m number of insulator rings, and a metallic ring-shaped spacer having an outwardly-extending left annular rim is welded to the right annular step of the first of the n number of insulator rings. Then, a distal end of the sleeve is welded to the ring-shaped spacer opposite the first of the n number of insulator rings.

In use, the AMD of the present invention is connectable to an implantable lead that extends from a proximal lead end having at least two spaced-apart first and second electrical contacts to a distal electrode that is configured for contact with body tissue. The lead opening in the end cap sidewall of the device housing is configured to receive the proximal end of the lead moved into the central lumen of the terminal housing assembly so that when the first and second lead contacts at the proximal lead end are in electrical continuity with the annular contact springs of respective ones of the n number of terminal housings, electrical continuity is established from the distal electrode of the lead to the annular contact springs of respective ones of the n terminal housings and to respective ones of the o jumper wires connected to respective ones of the x electrical contacts connected to respective ones of the y electronic components supported on the PCB. The lead is configured to at least one of deliver electrical stimulation to body tissue or sense biological signals from body tissue.

These and other aspects of the present invention will become increasingly more apparent to those skilled in the art by reference to the following detailed description and to the appended drawings.

DETAILED DESCRIPTION OF THE PREFERRED EMBODIMENTS

As used herein, the term "active medical device" means a medical device, whether implantable or worn externally, that is designed to deliver electrical stimulation to a patient or sense biological signals from body tissue, or both stimulate and sense.

As use herein, the term "fluid impermeable" means that the connection between two parts does not permit the passage of a fluid, for example, body fluid, through the connection. The connection can be a diffusion bonded connection between PVD-deposited titanium metallization and a titanium part, the weld connection between two metal parts, or the weld connection between a polymeric part and a metal part, for example, PEEK welded to titanium.

Figure 1:
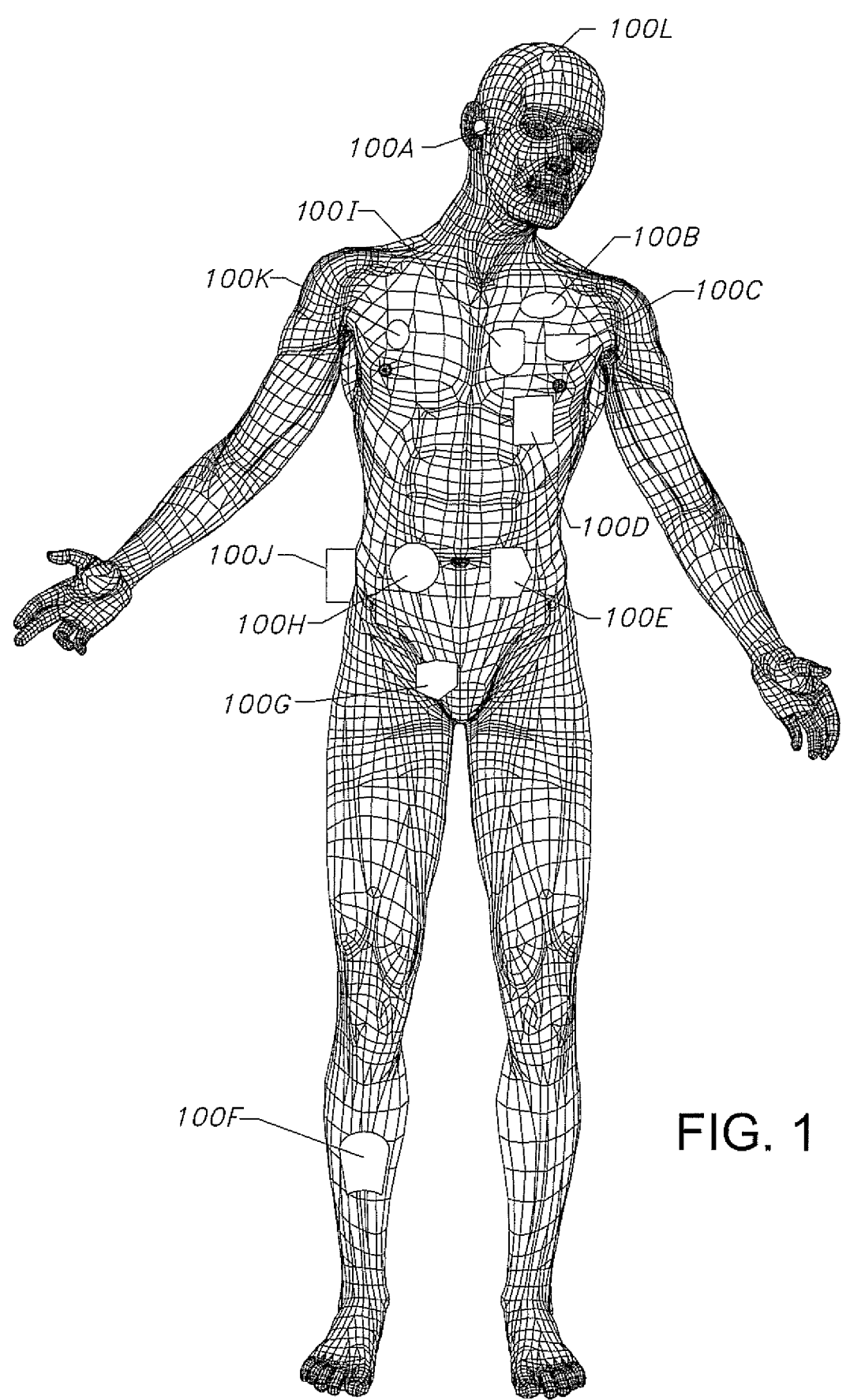
FIG. 1 is a wire-formed diagram of a generic human body showing a number of medical devices 100A to 100L according to the present invention that can either be implanted in a patient's body tissue or attached externally to the body.

Turning now to the drawings, FIG. 1 is a wire form diagram of a generic human body illustrating various types of active implantable and external medical devices according to the present invention that can either be implanted in a patient's body or attached externally to the body.

Numerical designation 100A represents a family of hearing devices which can include the group of cochlear implants, piezoelectric sound bridge transducers, and the like.

Numerical designation 100B represents a variety of neurostimulators, brain stimulators, and sensors. Neurostimulators are used to stimulate the Vagus nerve, for example, to treat epilepsy, obesity, and depression. Brain stimulators are pacemaker-like devices and include electrodes implanted deep into the brain for sensing the onset of a seizure and also providing electrical stimulation to brain tissue to prevent a seizure from actually occurring. The lead wires associated with a deep brain stimulator are often placed using real time MRI imaging. Sensors include optical sensors, motion sensors, acoustic sensors, pressure sensors, analyte sensors, and electromagnetic sensors, among others.

Numerical designation 100C shows a cardiac pacemaker which is well-known in the art.

Numerical designation 100D includes the family of left ventricular assist devices (LVADs), and artificial heart devices.

Numerical designation 100E includes a family of drug pumps which can be used for dispensing insulin, chemotherapy drugs, pain medications, and the like.

Numerical designation 100F includes a variety of bone growth stimulators for rapid healing of fractures.

Numerical designation 100G includes urinary incontinence devices.

Numerical designation 100H includes the family of pain relief spinal cord stimulators and anti-tremor stimulators.

Numerical designation 100H also includes an entire family of other types of neurostimulators used to block pain.

Numerical designation 100I includes a family of implantable cardioverter defibrillator (ICD) devices and also the family of congestive heart failure devices (CHF). This is also known in the art as cardio resynchronization therapy devices, otherwise known as CRT devices.

Numerical designation 100J illustrates an externally worn pack. This pack could be an external insulin pump, an external drug pump, an external neurostimulator or even a ventricular assist device.

Numerical designation 100K illustrates one of various types of EKG/ECG external skin electrodes which can be placed at various locations on the patient's body.

Numerical designation 100L represents external EEG electrodes that are placed on the patient's head.

Figure 2:
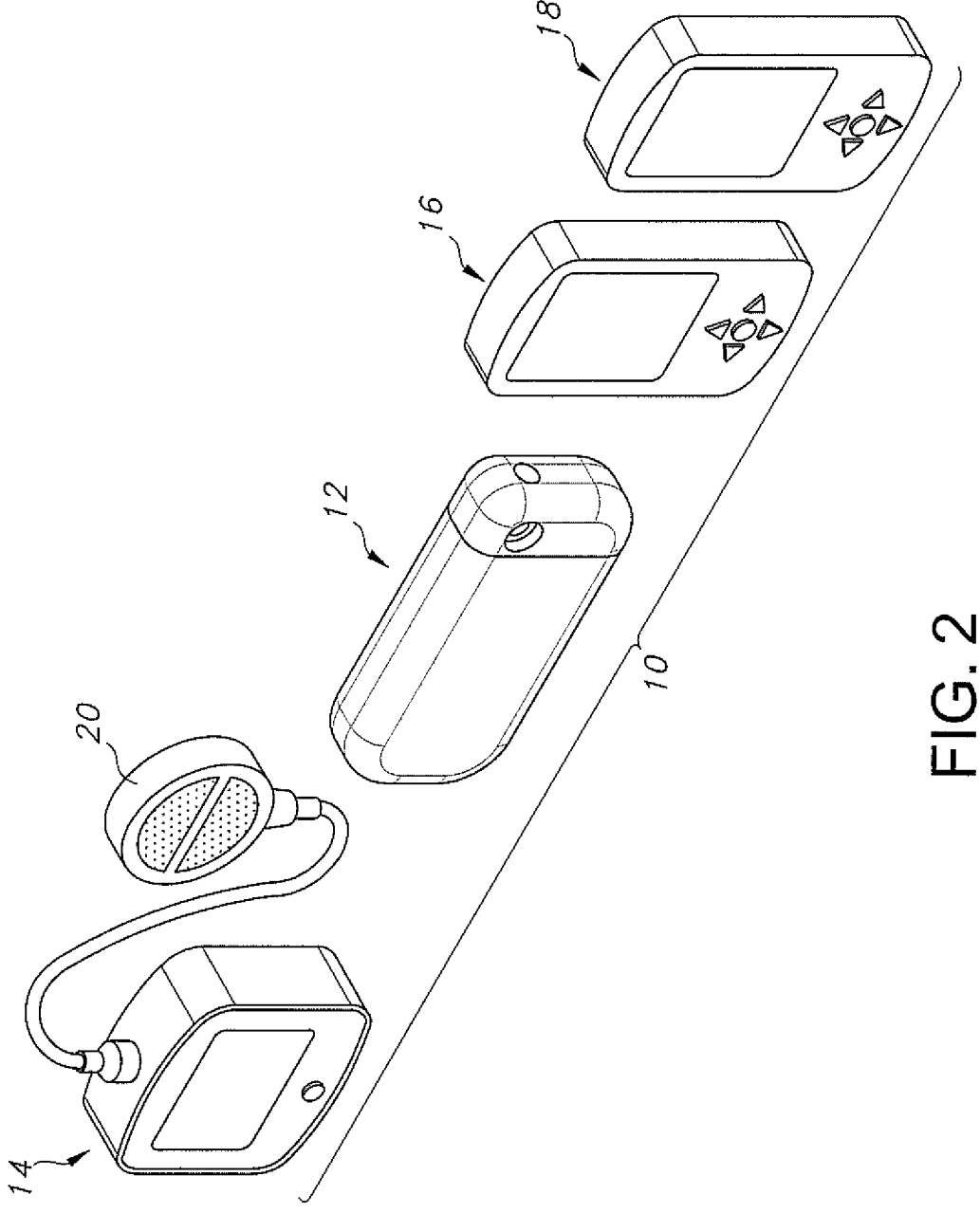
FIG. 2 is a simplified block diagram of an exemplary medical device system 10 according to the present invention.

To provide context to the various medical devices 100A to 100L illustrated in FIG. 1, FIG. 2 illustrates a simplified block diagram of an exemplary medical device system 10 according to the present invention. The medical device system 10 includes an active medical device (AMD) 12, which represents any of the various types of medical devices that include a lead, whether implantable or external, that are described above with reference to FIG. 1. If implantable, the lead is configured to at least one of deliver electrical stimulation to body tissue or sense biological signals from body tissue. The medical device system 10 also has an external charger 14, a patient programmer 16, and a clinician programmer 18.

The patient programmer 16 and the clinician programmer 18 may be portable handheld devices, such as a smartphone or other custom device, that are used to configure the AMD 12 so that the AMD can operate in a desired manner. The patient programmer 16 is used by the patient in whom the AMD 12 is implanted. The patient may adjust the parameters of electrical stimulation delivered by the AMD 12, such as by selecting a stimulation program, changing the amplitude and frequency of the electrical stimulation, among other parameters, and by turning stimulation on and off. Additionally, the patient programmer 16 may collect and display data being collected by the device 12 and alert the patient to potential health risks.

The clinician programmer 18 is used by medical personnel to configure the other system components and to adjust stimulation parameters that the patient is not permitted to control. These include setting up stimulation programs among which the patient may choose and setting upper and lower limits for the patient's adjustments of amplitude, frequency, and other parameters. It is also understood that although FIG. 2 illustrates the patient programmer 16 and the clinician programmer 18 as two separate devices, they may be integrated into a single programmer in some embodiments.

Electrical power can be delivered to the AMD 12 through an external charging pad 20 that is connected to the external charger 14. In some embodiments, the external charging pad 20 is configured to directly power the AMD 12 or it is configured to charge a rechargeable electrical power source 22 (FIG. 3) of the AMD. The external charging pad 20 can be a hand-held device that is connected to the external charger 14, or it can be an internal component of the external charger. The external charger 14 and the charging pad 20 can also be integrated into a single device that is strapped on or attached to the patient with adhesive, and the like.

Figures 3, 3A:
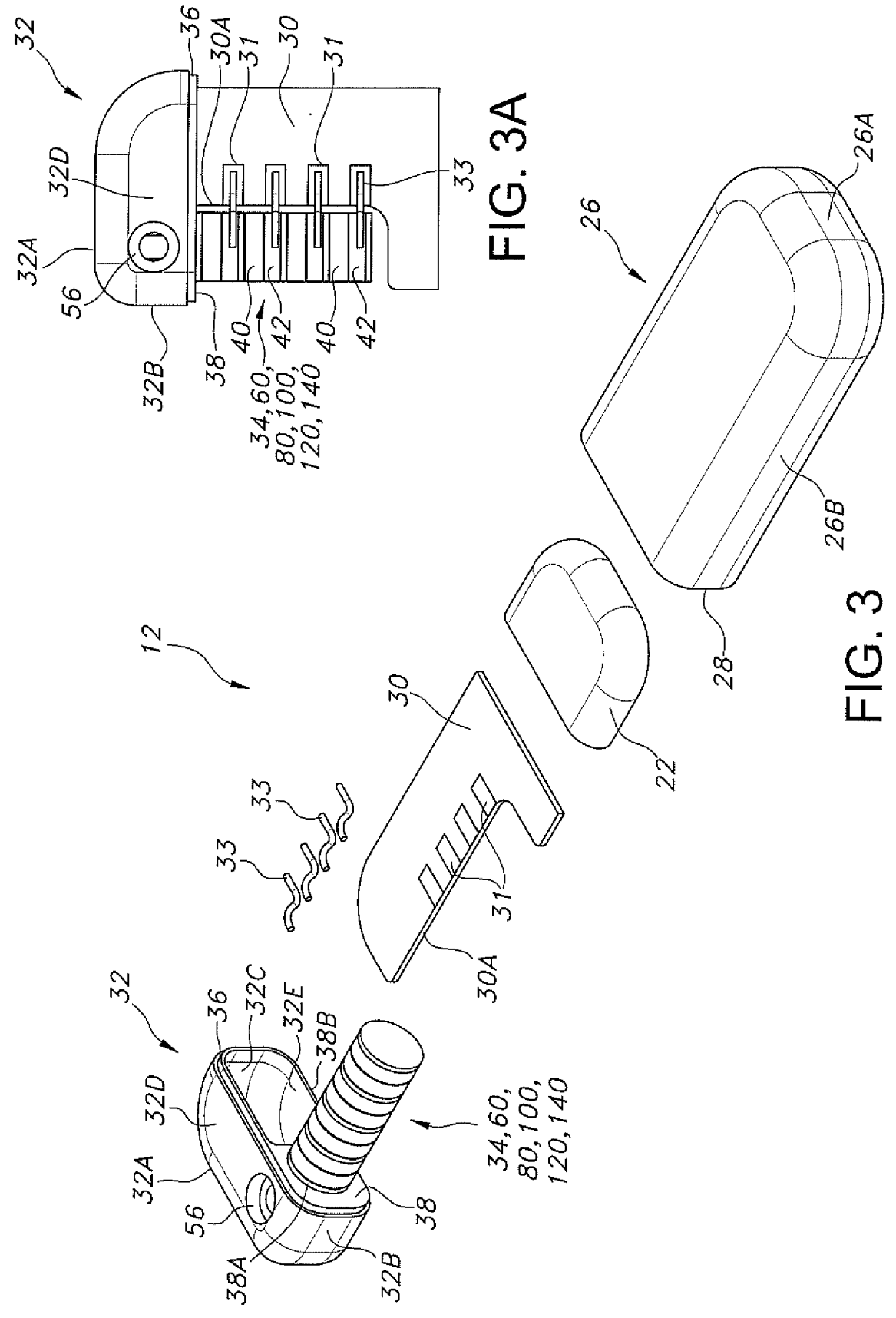
FIG. 3 is a broken-apart view of an exemplary active medical device (AMD) 12, which is any of various types of the AMDs that are shown in FIG. 1.
FIG. 3A is a side view of a terminal housing assembly 34, 60, 80, 100, 120 and 140 connected to a printed circuit board (PCB) 30 according to the present invention.

Referring now to FIG. 3, this drawing illustrates the AMD 12 as an exemplary embodiment of the various medical devices 100A to 100L illustrated in FIG. 1 and the exemplary AMD 12 shown in the medical device system 10 in FIG. 2 that can be implanted in a patient's body or worn externally on a patient's body. The AMD 12 comprises a main housing 26 that is closed by an end cap 32 to provide a device housing for the AMD. As will be described in greater detail hereinafter, the end cap 32 supports any one of a number of terminal housing assemblies 34, 60, 80, 100, 120 and 140.

The main housing 26 comprises a curved end wall 26A extending to opposed planar edge walls 26B (the opposite edge wall to wall 26B is not shown) and opposed planar face walls 26C (the opposite face wall to wall 26C is not shown). Curved intermediate sidewalls connect to the opposed housing edge walls, to the opposed housing face walls, and to the housing bottom wall. In turn, the opposed edge walls, face walls and intermediate curved sidewalls extend to an annular upper edge 28 surrounding an opening leading into an interior of the main housing 26. Titanium is a preferred material for the main housing 26.

A printed circuit board (PCB) assembly 30 comprising a PCB supporting at least two electronic circuits or electronic components (not shown) is housed inside the main housing 26. The main housing 26 also contains the electrical power source 22 connected to the PCB assembly 30 to provide electrical power to the at least two electronic circuits or electronic components. The PCB assembly 30 in turn provides electrical power to a lead (not shown) that is detachably connected to the terminal housing assemblies 34, 60, 80, 100, 120 and 140. As is well understood by those skilled in the art, the lead has a number of electrodes that are configured to deliver current pulses to body tissue in which the AMD 12 is implanted, receive sensed electrical signals pertaining to functions of the body tissue, or both sense electrical signals and deliver current pulses.

The electrical power source 22 for the AMD 12 can be a capacitor or a rechargeable battery, for example a hermetically sealed rechargeable Li-ion battery. However, the electrical power source 22 is not limited to any one chemistry or even a rechargeable chemistry and can be of an alkaline cell, a primary lithium cell, a rechargeable lithium-ion cell, a Ni/cadmium cell, a Ni/metal hydride cell, a supercapacitor, a thin film solid-state cell, and the like. Preferably, the electrical power source 22 is a lithium-ion electrochemical cell comprising a carbon-based or $Li_4Ti_5O_{12}$-based anode and a lithium metal oxide-based cathode, such as of $LiCoO_2$ or lithium nickel manganese cobalt oxide ($LiNi_aMn_bCo_{1-a-b}O_2$). The electrical power source 22 can also be a solid-state thin film electrochemical cell having a lithium anode, a metal-oxide based cathode and a solid electrolyte, such as an electrolyte of LiPON ($Li_xPO_yN_z$).

8

Figure 4:
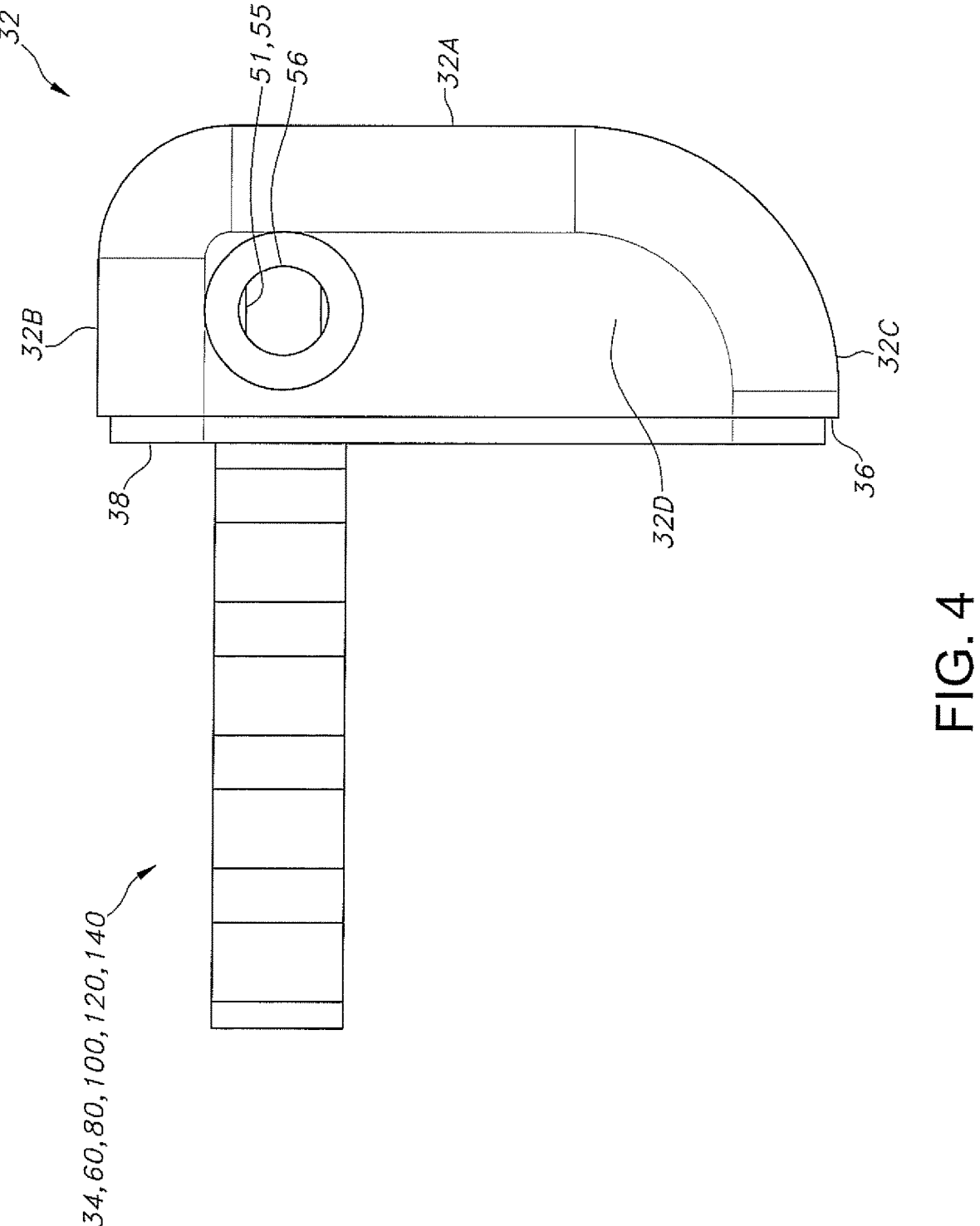
FIG. 4 is an enlarged elevational view of a lead connector assembly 24 for the AMD shown in FIGS. 2 and 3.
Figure 5:
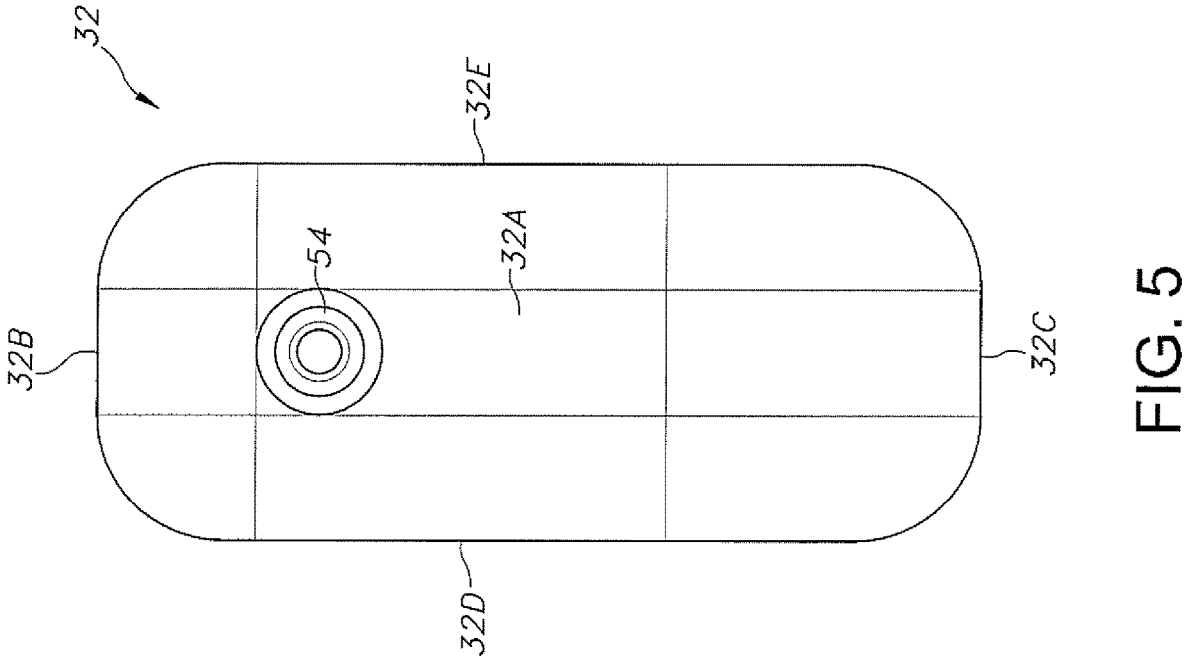
FIG. 5 is an end elevational view of the lead connector assembly 24 shown in FIG. 4.

As shown in FIGS. 3 to 5, the end cap 32 comprises a curved end wall 32A extending to a planar upper edge walls 32B opposite a curved lower edge wall 32C and opposed planar face walls 32D and 32E. Curved intermediate side-walls connect to the opposed cap upper and lower edge walls 32B, 32C, to the opposed cap left and right face walls 32D, 32E, and to the cap end wall 32A. In turn, the opposed upper and lower edge walls 32B, 32C, left and right face walls 32D, 32E and the intermediate curved sidewalls extend to an annular edge 36 surrounding an opening leading into the interior of the end cap 32. A cap plate 38 is connected to the annular edge 36 of the end cap 32. The cap plate 38 has a minor circular opening 38A and a major opening 38B leading into the interior of the end cap 32. The annular edge 36 of the end cap 32 adjacent to the cap plate 38 is connected to the upper annular edge 28 of the main housing 26 to provide a hermetically closed device housing containing the electrical power source 22 connected to the PCB assembly 30.

Figure 6:
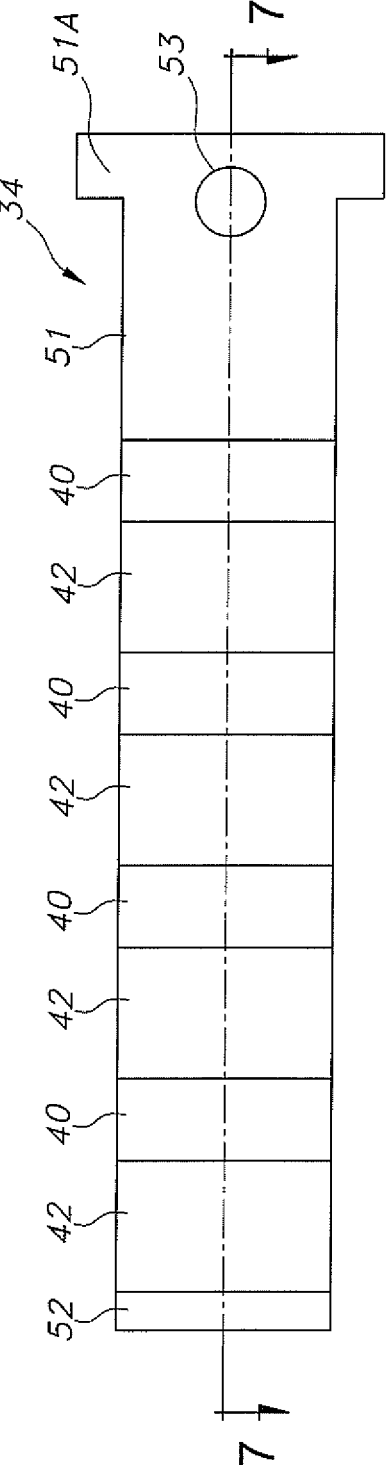
FIG. 6 is a schematic view of an exemplary embodiment of the terminal housing assembly 34 shown in FIGS. 3 and 4 in greater detail.
Figure 7:
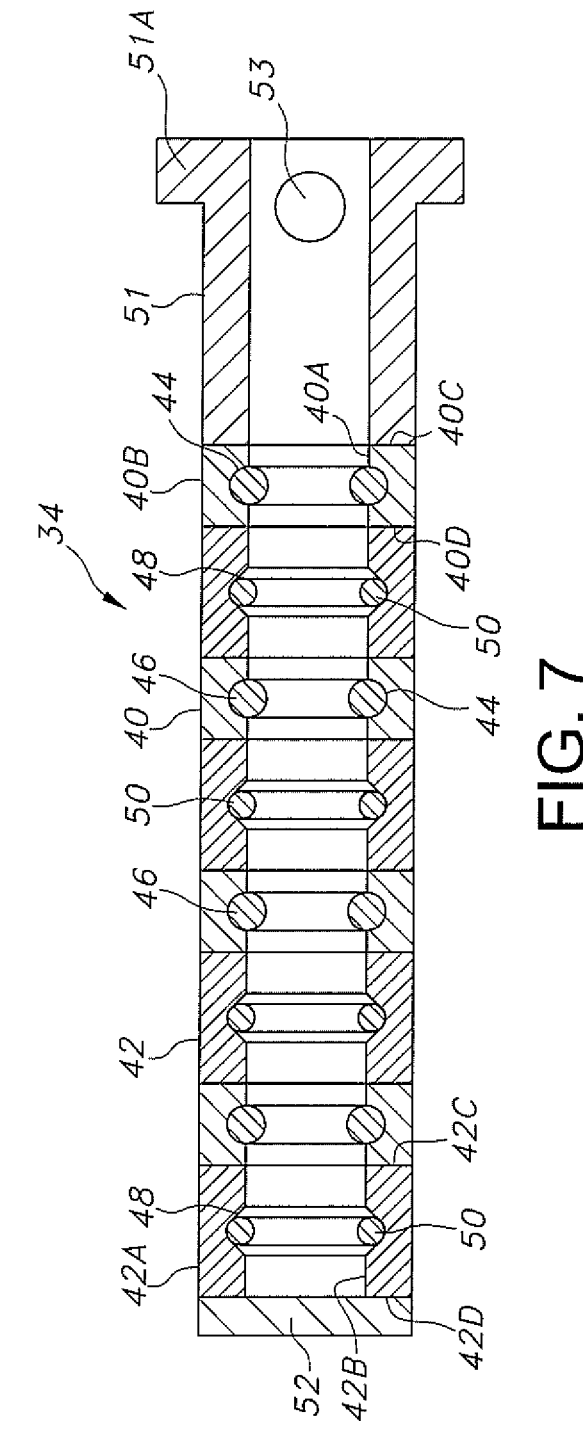
FIG. 7 is a cross-sectional view taken along line 7-7 of FIG. 6.

FIGS. 6 and 7 illustrate one exemplary embodiment of the terminal housing assembly 34 shown in FIGS. 3 and 4 in greater detail. The terminal housing assembly 34 is comprised of alternating polymeric insulator rings 40 and metallic terminal housings 42. Each of the polymeric insulator rings 40 has an annularly-shaped, preferably cylindrically-shaped, inner wall 40A that is co-axially aligned with an annularly-shaped, preferably cylindrically-shaped, outer wall 40B. The inner and outer walls 40A, 40B extend to spaced-apart right and left planar sidewalls 40C and 40D. An inner annular groove 44 having a semi-circular shape in cross-section resides in the inner wall 40A, centered between the right and left sidewall 40C, 40D.

A compliant polymeric ring seal in the shape of an O-ring 46 is seated in the inner annular groove 44. The O-ring 46 has a portion that extends into the lumen formed by the inner wall 40A. Polyether ether ketone (PEEK) is a preferred material for the polymeric insulator rings 40. Silicone is a preferred material for the O-ring 46.

While PEEK is a preferred material for the polymeric insulator rings 40, the rings may be formed from any suitable polymer or combination of polymers that are bio-compatible and suitable for implantation in a patient. In some examples, the polymer material may have a relatively low permeability (e.g., to form a fluid impermeable barrier). The polymeric insulator rings 40 may be formed of a polymeric material that melts when heated, e.g., by heat transferred to the polymeric insulator rings 40 from the metallic terminal housings 42 along the interface where they contact each other. In some examples, the polymeric insulator rings 40 may be formed of a polymer that is able to reflow and solidify without significant degradation. In some examples, the polymer may be a thermoplastic.

In some examples, the polymeric insulator rings 40 include a single polymer material. In other examples, the polymeric insulator rings 40 include a combination of polymers. In addition to PEEK, suitable polymers are selected from polysulfone, polyetherimide, polyphenylsulfone, ultra-high molecular weight (UHMW) polyethylene (PE), and polyethersulfone (PES). Other suitable polymers include those that are liquid crystalline polymers (LCPs), which may be highly adaptable to AMD applications. In some examples, the polymeric insulator rings 40 include at least one polymeric polymer. In some examples, polyolefins and/or silicones may be used for the polymeric insulator rings 40.

In some examples, the polymeric insulator rings 40 may be formed from a bulk or main polymer portion (e.g., PEEK or LCP) with a layer of a second polymer material (e.g., a suitable thermoplastic) that has a lower melting temperature in the area of contact with the metallic terminal housings 42 (e.g., at the interface where the insulator rings 40 and the terminal housings 42 contact each other). In some examples, the second polymer material may be referred to a "tie layer," and when melted and cooled, may have better adhesive properties to the metallic terminal housings 42 than the bulk material to ensure a better bond with the metallic housings 42.

The metallic terminal housings 42 comprise an annularly-shaped, preferably cylindrically-shaped, inner wall 42A that is co-axially aligned with an annularly-shaped, preferably cylindrically-shaped, outer wall 42B. The inner and outer walls 42A, 42B extend to spaced-apart right and left planar sidewalls 42C and 42D. An inner annular groove 48 having a semi-circular shape in cross-section resides in the inner wall 42A, centered between the right and left sidewalls 42C, 42D. An annular metallic contact spring 50 is seated in the annular groove 48. A suitable contact spring 50 is a BAL SEAL® type canted coil spring (BAL SEAL is a registered trademark of Bal Seal Engineering Co., Inc.).

To construct the terminal housing assembly 34, a first or proximal-most metallic terminal housing 42 supporting a contact spring 50 seated in the inner annular groove 48 is welded to the left sidewall 40D of a first or proximal-most polymeric insulator ring 40. Preferably, a polymeric O-ring 46 is seated in the inner annular groove 44 before the polymeric insulator ring 40 is welded to the terminal housing 42. A second polymeric insulator ring 40 supporting a polymeric O-ring 46 is then welded to the left sidewall 42D of the first terminal housing 42. A second metallic terminal housing 42 supporting a contact spring 50 is welded to the left sidewall 40D of the second insulator ring 40. A third polymeric insulator ring 40 supporting a polymeric O-ring 46 is then welded to the left sidewall 42D of the second metallic terminal housing 42, followed by a third metallic terminal housing 42 supporting a contact spring 50 being welded to the left sidewall 40D of the third polymeric insulator ring 40. This sequence continues until the terminal housing assembly 34 has the desired number of alternating polymeric insulator rings 40 supporting a polymeric O-ring 46 and metallic terminal housings 42 supporting a contact spring 50 welded one to the other. Preferably, there are from 2 to 24 insulator rings 40 connected to 2 to 24 terminal housings 42 in an alternating configuration as described above.

To complete the terminal housing assembly 34, the distal end of a metallic sleeve 51 is welded to the right sidewall 40C of the first or proximal-most polymeric insulator ring 40 and a metallic terminal plate 52 is welded to the left sidewall 42D of the distal-most metallic terminal housing 42.

The sleeve 51 also has a proximal flange 51A. This flange is welded to the inner surface of the end wall 32A of the end cap 32. This positions the main body of the terminal housing assembly 34 extending distally, out past the annular edge 36 of the end cap 32 and through the minor opening 38A in the cap plate 38. That way, the longitudinal axis of the terminal housing assembly 34 is aligned at an orientation that is substantially perpendicular to the planar cap plate 38 and substantially perpendicular to an imaginary plane aligned along the annular edge 36 of the end cap 32. A lead opening 54 (FIG. 5) in the curved end wall 32A of the end cap 32 is aligned with the lumen extending through the terminal housing assembly 34. This lumen ends at the terminal plate 52. Further, the sleeve 51 has a lateral opening 53 that aligns with a lateral treaded opening 56 in the end cap 32 (FIGS.

3 to 5). Laser or ultrasonically welding are preferred techniques for all of the welded connections. Titanium is a preferred material for the sleeve 51 and terminal plate 52.

FIG. 3A shows that the PCB assembly 30 has an edge 30A that extends along an edge axis. A plurality of spaced-apart electrical contacts 31 extend to this edge. The electrical contacts are connected to the previously described at least two electronic circuits or electronic components.

A proximal portion of the PCB assembly 30 is moved through the major opening 38B in the cap plate 38 and into the interior of the end cap 32. In this position, the edge axis is parallel to the central axis of the lumen that extends through the sleeve 51 connected to the alternating insulator rings 40 and terminal housings 42 of the terminal housing assembly 34. Further, the spaced-apart electrical contacts 31 of the PCB assembly 30 are aligned with the metallic terminal housings 42 of the lead connector assembly 34. Jumper wires 33 connect an individual terminal housing 42 to a corresponding electrical contact 31. The PCB assembly 30 is also connected to the electrical power source 22. In that manner, electrical continuity is established from the at least two electronic circuits or electronic components (not shown) supported on the PCB assembly 30 to the individual terminal housings 42 of the terminal housing assembly 34. That is without there being a feedthrough connecting between the terminal housing assembly 34 and the PCB assembly 30. Feedthroughs are well known by those skilled in the art.

In use, the proximal end of a lead (not shown) is moved through the lead opening 54 (FIG. 5) in the curved end wall 32A of the end cap 32, through the metallic sleeve 51 and into the lumen provided by the terminal housing assembly 34 so that electrical contacts at the proximal end of the lead are aligned with and electrically connected to the canted coil springs 46 of the terminal housings 42. FIG. 4 shows that the left face wall 32D of the end cap 32 has a lateral treaded opening 56 that is sized to receive a threaded fastener (not shown) that intersects the lateral opening 53 in the sleeve 51. That way, the fastener threaded into the aligned openings 56 and 53 contacts the proximal end of a lead to secure the lead received in the terminal housing assembly 34 in place. The polymeric O-rings 46 of the polymeric insulator rings 40 help prevent ingress of body fluid, and the like, through the end cap 32 to the metallic terminal housings 44 of the terminal housing assembly 40. In that respect, with the sleeve 51 welded to the inner surface of the end cap 32, body fluid could flow into the lumen of the terminal housing assembly 34, but the assembly 34 is impermeable to body fluid flowing through the connected insulator rings 40 and terminal housings 42 and into the interior of the device housing formed by the end cap 32 connected to the main housing 26.

Figures 8, 8A:
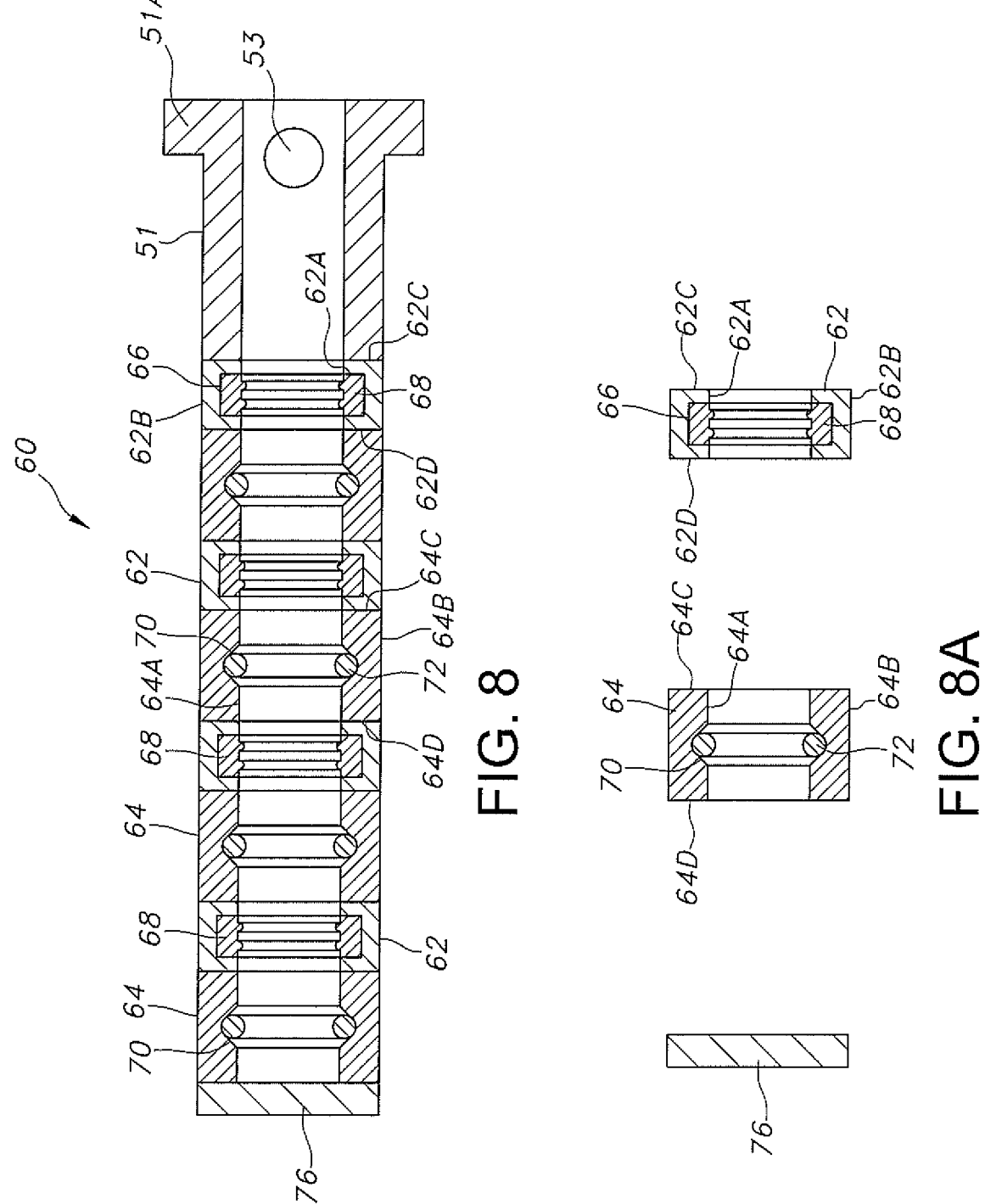
FIG. 8 is a cross-sectional view of another exemplary embodiment of the terminal housing assembly 60 shown in FIGS. 3 and 4.
FIG. 8A is a broken-apart view showing a polymeric insulator ring 62 housing a polymeric ring seal 68, a terminal housing 64 for a metallic annular contact spring 72, and a terminal plate 76 for the terminal housing assembly 60 shown in FIG. 8.

FIGS. 8 and 8A illustrate another exemplary embodiment of a terminal housing assembly 60 according to the present invention. This terminal housing assembly 60 is comprised of alternating polymeric insulator rings 62 and ring-shaped metallic terminal housings 64. However, unlike the polymeric insulator rings 40 for the terminal housing assembly 34 described with respect to FIGS. 6 and 7, the insulator rings 62 are made from a machined ceramic, preferably alumina.

Each of the ring-shaped ceramic insulator rings 62 has an annularly-shaped, preferably cylindrically-shaped, inner wall 62A that is co-axially aligned with an annularly-shaped, preferably cylindrically-shaped, outer wall 62B. The inner and outer walls 62A, 62B extend to spaced-apart right and left planar sidewalls 62C and 62D. An inner annular groove 66 having a square- or rectangular-shape in cross-section resides in the inner wall 62A, centered between the right and left sidewalls 62C, 62D. A compliant polymeric ring seal 68 is seated in the inner annular groove 66. The polymeric ring seal 68 has a square- or rectangular-shaped base that seats in the inner annular groove 66 and an inwardly-extending pair of side-by-side annular protrusions that serve as side-by-side seals. Silicone is a preferred material for the polymeric ring seal 68.

The ring-shaped metallic terminal housings 64 comprise an annularly-shaped, preferably cylindrically-shaped, inner wall 64A that is co-axially aligned with an annularly-shaped, preferably cylindrically-shaped, outer wall 64B. The inner and outer walls 64A, 64B extend to spaced-apart right and left planar sidewalls 64C and 64D. An inner annular groove 70 having a semi-circular shape in cross-section resides in the inner wall 64A, centered between the right and left sidewalls 64C, 64D. A metallic annular contact spring 72 is seated in the annular groove 70. A suitable contact spring 72 is a BAL SEAL® type canted coil spring. Titanium is a preferred material for the terminal housings 64.

To construct the terminal housing assembly 60, the right and left sidewalls 62C, 62D of the desired number of ceramic insulator rings 62 are coated with a titanium metallization, preferably using a physical vapor deposition (PVD) process. Then, the titanium metallized left sidewall 62D of a first ceramic insulator ring 62 is contacted to the right sidewall 64C of a first titanium terminal housing 64. Next, the titanium coated right sidewall 62C of a second ceramic insulator ring 62 is contacted to the left sidewall 64D of the first titanium terminal housing 64. This is followed by the right sidewall 64C of a second titanium terminal housing 64 being contacted to the left sidewall 62D of the second ceramic insulator ring 62. The desired number of insulator rings 62 and terminal housings 64 are contacted to each other in this manner. Then, the proximal metallic sleeve 51 is contacted to the titanium coated right sidewall 62C of the first or proximal-most ceramic insulator ring 62 and the metallic terminal plate 76 is contacted to the left sidewall 64D of the distal-most metallic terminal housing 64 to complete the terminal housing assembly 60. Preferably, there are from 2 to 24 insulator rings 62 connected to 2 to 24 terminal housings 64 in an alternating configuration as described above.

This assembly is then subjected to an axial pressure aligned along the axis of the terminal housing assembly 60 ranging from about 1 MPa to about 5 MPa at a temperature ranging from about 850° C. to about 950° C. for up to about 2 hours. This serves to diffusion bond the PVD-deposited titanium metallization contacting the left sidewalls 62D of the ceramic insulator rings 62 to the right sidewalls 64C of the metallic terminal housings 64, to diffusion bond the PVD-deposited titanium metallization contacting the right sidewalls 62C of the ceramic insulator rings 62 to the left sidewalls 64D of the metallic terminal housings 64, to diffusion bond the proximal metallic sleeve 51 to the titanium coated right sidewall 62C of the first ceramic insulator ring 62, and to diffusion bond the metallic terminal plate 76 to the left sidewall 64D of the distal-most metallic terminal housing 64 together. After this diffusion bonding takes place, a silicone ring seal 68 is seated in the inner annular groove 66 of each of the ceramic insulator rings 62 and a canted coil spring 72 is seated in the inner annular groove 70 of each of the terminal housings 64.

In a similar manner as described above with respect to the terminal housing assembly 34 shown in FIGS. 6 and 7, the flange 51A of the proximal metallic sleeve 51 is welded to the inner surface of the end wall 32A of the end cap 32 with the main body of the terminal housing assembly 60 extending distally, out past the annular edge 36 of the end cap 32 and through the minor opening 38A in the cap plate 38. This aligns the longitudinal axis of the terminal housing assembly 60 at an orientation that is substantially perpendicular to the planar face of the cap plate 38 and substantially perpendicular to an imaginary plane aligned along the annular edge 36 of the end cap 32.

In use, the proximal end of a lead (not shown) is moved through the lead opening 54 (FIG. 5) in the curved end wall 32A of the end cap 32, through the metallic sleeve 51 and into the lumen provided by the terminal housing assembly 60. In this position, electrical contacts at the proximal end of the lead are aligned with and electrically connected to the annular contact springs 72 of terminal housings 64. A fastener is threaded through the treaded opening 56 in the end cap 32 to intersect the lateral opening 53 in the sleeve 51 until the threaded fastener contacts the lead to secure the proximal end of the lead received in the terminal housing assembly 60 in place. The ring seals 88 of the ceramic insulator rings 82 help prevent ingress of body fluid, and the like, through the end cap 32 to the metallic terminal housings 64 of the terminal housing assembly 60. In that respect, with the sleeve 51 welded to the inner surface of the end cap 32, body fluid could flow into the lumen of the terminal housing assembly 60, but the assembly 60 is impermeable to body fluid flowing through the connected insulator rings 62 and terminal housings 64 and into the interior of the device housing formed by the end cap 32 connected to the main housing 26.

Figures 9, 9A:
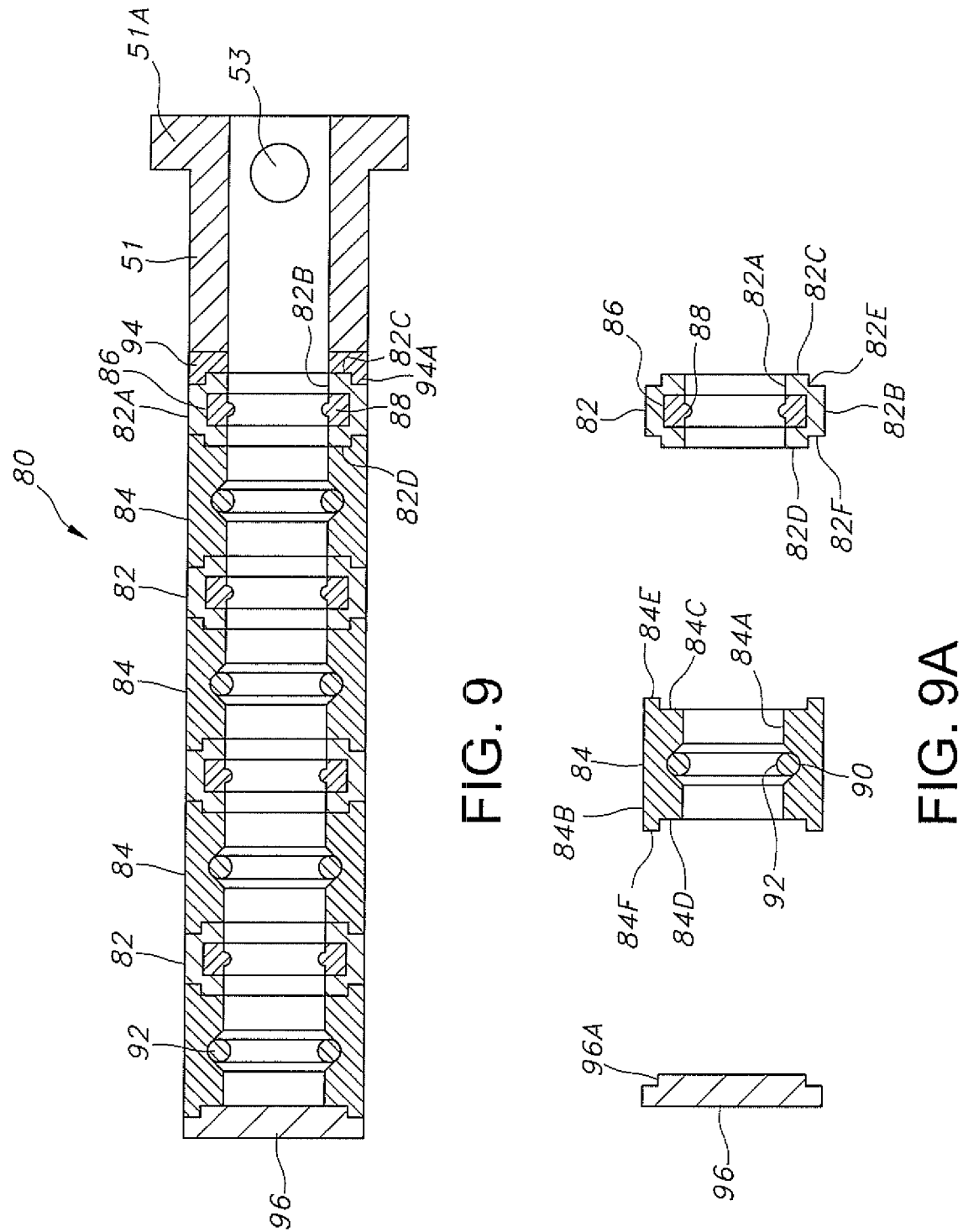
FIG. 9 is a cross-sectional view of another exemplary embodiment of the terminal housing assembly 80 shown in FIGS. 3 and 4.
FIG. 9A is a broken-apart view showing a polymeric insulator ring 82 housing a polymeric ring seal 68, a metallic terminal housing 84 for a metallic annular contact spring 92, and a terminal plate 96 for the terminal housing assembly 80 shown in FIG. 9.

FIGS. 9 and 9A illustrate another exemplary embodiment of a terminal housing assembly 80 according to the present invention. This assembly 80 is comprised of alternating ceramic insulator rings 82 and ring-shaped metallic terminal housings 84. Each of the ceramic insulator rings 82 has an annularly-shaped, preferably cylindrically-shaped, inner wall 82A that is co-axially aligned with an annularly-shaped, preferably cylindrically-shaped, outer wall 82B. The inner and outer walls 82A, 82B extend to spaced-apart right and left sidewalls 82C and 82D. The sidewalls 82C, 82D are provided with respective inwardly-extending right and left annular steps 82E and 82F adjacent to the outer wall 82B. An inner annular groove 86 having a square- or rectangular-shape in cross-section resides in the inner wall 82A, centered between the right and left sidewalls 82C, 82D. A compliant polymeric ring seal 88 has a square- or rectangular-shaped base that seats in the inner annular groove 86 and a centered, inwardly-extending annular protrusion that serves as a seal. Alumina is a preferred material for the ceramic insulator rings 82 and silicone is a preferred material for the polymeric ring seal 88.

The ring-shaped metallic terminal housings 84 comprise an annularly-shaped, preferably cylindrically-shaped, inner wall 84A that is co-axially aligned with an annularly-shaped, preferably cylindrically-shaped, outer wall 84B. The inner and outer walls 84A, 84B extend to spaced-apart right and left sidewalls 84C and 84D. The sidewalls 84C, 84D are provided with respective outwardly-extending annular right and left rims 84E and 84F adjacent to the outer wall 84B. An inner annular groove 90 having a semi-circular shape in cross-section resides in the inner wall 84A, centered between the right and left sidewalls 84C, 84D. A metallic annular contact spring 92 is seated in the annular groove 90. A suitable contact spring 92 is a BAL SEAL® type canted coil spring. Titanium is a preferred material for the terminal housings 84.

To construct the terminal housing assembly 80, the right and left sidewalls 82C, 82D including the annular steps 82E, 82F of the desired number of ceramic insulator rings 82 are coated with a titanium metallization, preferably using a physical vapor deposition (PVD) process. Then, the titanium coated left sidewall 82D of a first ceramic insulator ring 82 is contacted to the right sidewall 84C of a first metallic terminal housing 84 with the outwardly-extending annular rim 84E received in the inner annular step 82F of the insulator ring 82. Next, the titanium coated right sidewall 82C of a second ceramic insulator ring 82 is contacted to the left sidewall 84D of the first metallic terminal housing 84 with the outwardly-extending rim 84F received in the inwardly-extending step 82E of the insulator ring. This is followed by the right sidewall 84C of a second metallic terminal housing 84 being contacted to the left sidewall 82D of the second ceramic insulator ring 82 with the outwardly-extending annular rim 84E received in the inner annular step 82F of the insulator ring 82. The desired number of insulator rings 82 and terminal housings 84 are contacted to each other in this manner. Further, the distally facing annular rim 94A of a proximal metallic ring-shaped spacer 94, preferably made of titanium, is received in the annular right step 82E of the first or proximal-most ceramic insulator ring 82. Preferably, there are from 2 to 24 insulator rings 82 connected to 2 to 24 terminal housings 84 in an alternating configuration as described above.

This assembly is then subjected to an axial pressure aligned along the axis of the terminal housing assembly 80 ranging from about 1 MPa to about 5 MPa at a temperature ranging from about 850° C. to about 950° C. for up to about 2 hours. This serves to diffusion bond the PVD-deposited titanium metallization contacting the left sidewalls 82D of the ceramic insulator rings 82 to the right sidewalls 84C of the metallic terminal housings 84, diffusion bond the PVD-deposited titanium metallization contacting the right sidewalls 82C of the ceramic insulator rings 82 to the left sidewalls 84D of the metallic terminal housings 84, and diffusion bond the annular rim 94A of the proximal metallic ring-shaped spacer 94 to PVD-deposited titanium metallization contacting the right sidewall 82C of the proximal-most ceramic insulator ring 82. A benefit attributed to the mating annular rims 84E, 84F received in the annular steps 82F, 82E is that this construction prevents the ceramic insulator rings 82 and terminal housings from slipping laterally with respect to each other when the assembly is subjected to the axial pressure discussed above.

After this diffusion bonding takes place, a silicone ring seal 68 is seated in the inner annular groove 66 of each of the ceramic insulator rings 62 and a canted coil spring 72 is seated in the inner annular groove 70 of each of the terminal housings 64.

Then, the proximal metallic sleeve 51 is welded to the proximal metallic ring-shaped spacer 94. A terminal plate 96 is welded to the left sidewall 84D of the distal-most metallic terminal housing 64. The terminal plate 96 has an inwardly-extending step 96A that receives the outwardly-extending annular rim 84F of the terminal housing 84 to complete the terminal housing assembly 80.

In a similar manner as described above with respect to the terminal housing assembly 34 shown in FIGS. 6 and 7, the flange 51A of the proximal metallic sleeve 51 is welded to the inner surface of the end wall 32A of the end cap 32 with the main body of the terminal housing assembly 80 extending distally, out past the annular edge 36 of the end cap 32 and through the minor opening 38A in the cap plate 38. This aligns the longitudinal axis of the terminal housing assembly

80 at an orientation that is substantially perpendicular to the planar face of the cap plate 38 and substantially perpendicular to an imaginary plane aligned along the annular edge 36 of the end cap 32.

In use, the proximal end of a lead (not shown) is moved through the lead opening 54 (FIG. 5) in the curved end wall 32A of the end cap 32, through the metallic sleeve 51 and into the lumen provided by the terminal housing assembly 80 so that electrical contacts at the proximal end of the lead are aligned with and electrically connected to the canted coil springs 92 of the terminal housings 84. A fastener is threaded through the treaded opening 56 in the end cap 32 to intersect the lateral opening 53 in the sleeve 51 until the threaded fastener contacts the lead to secure the proximal end of the lead received in the terminal housing assembly 34 in place. The ring seals 88 of the ceramic insulator rings 82 help prevent ingress of body fluid, and the like, through the end cap 32 to the metallic terminal housings 84 of the terminal housing assembly 80. In that respect, with the sleeve 51 welded to the inner surface of the end cap 32, body fluid could flow into the lumen of the terminal housing assembly 80, but the assembly 80 is impermeable to body fluid flowing through the connected insulator rings 82 and terminal housings 84 and into the interior of the device housing formed by the end cap 32 connected to the main housing 26.

Figure 9B:
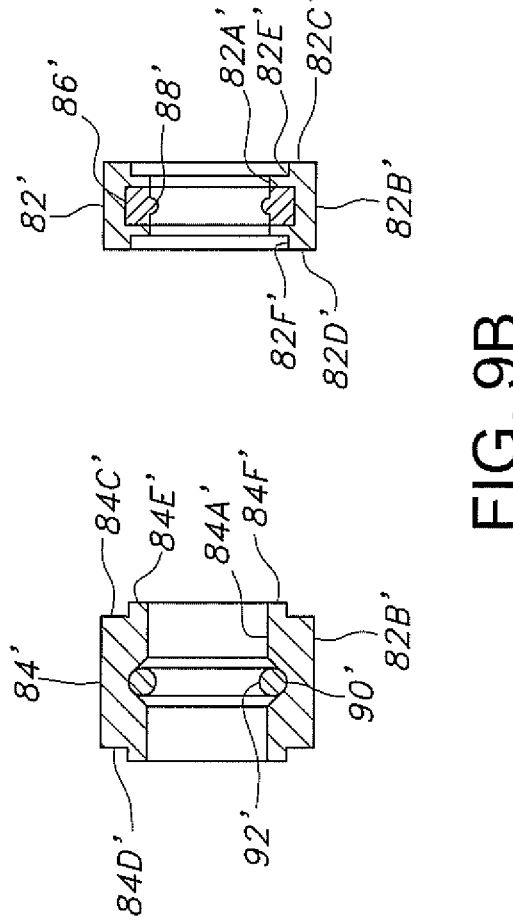
FIG. 9B illustrates an alternate embodiment of a ceramic insulator ring 82' connected to a ring-shaped metallic terminal housings 84'.

FIG. 9B illustrates an alternate embodiment of the ceramic insulator rings 82' having an annularly-shaped, preferably cylindrically-shaped, inner wall 82A' that is co-axially aligned with an annularly-shaped, preferably cylindrically-shaped, outer wall 82B'. The inner and outer walls 82A', 82B' extend to spaced-apart right and left sidewalls 82C' and 82D'. The sidewalls 82C', 82D' are provided with respective inwardly-extending right and left annular steps 82E' and 82F' adjacent to the inner wall 82A'. An inner annular groove 86' having a square- or rectangular-shape in cross-section resides in the inner wall 82A', centered between the right and left sidewalls 82C', 82D'. A compliant polymeric ring seal 88' has a square- or rectangular-shaped base that seats in the inner annular groove 86' and a centered, inwardly-extending annular protrusion that serves as a seal. Alumina is a preferred material for the ceramic insulator rings 82' and silicone is a preferred material for the polymeric ring seal 88'.

The ring-shaped metallic terminal housings 84' comprise an annularly-shaped, preferably cylindrically-shaped, inner wall 84A' that is co-axially aligned with an annularly-shaped, preferably cylindrically-shaped, outer wall 84B'. The inner and outer walls 84A', 84B' extend to spaced-apart right and left sidewalls 84C' and 84D'. The sidewalls 84C', 84D' are provided with respective outwardly-extending annular right and left rims 84E' and 84F' adjacent to the inner wall 84A'. An inner annular groove 90' having a semi-circular shape in cross-section resides in the inner wall 84A', centered between the right and left sidewalls 84C', 84D'. A metallic annular contact spring 92' is seated in the annular groove 90'. A suitable contact spring 92' is a BAL SEAL® type canted coil spring. Titanium is a preferred material for the terminal housings 84'.

Figures 10, 10A:
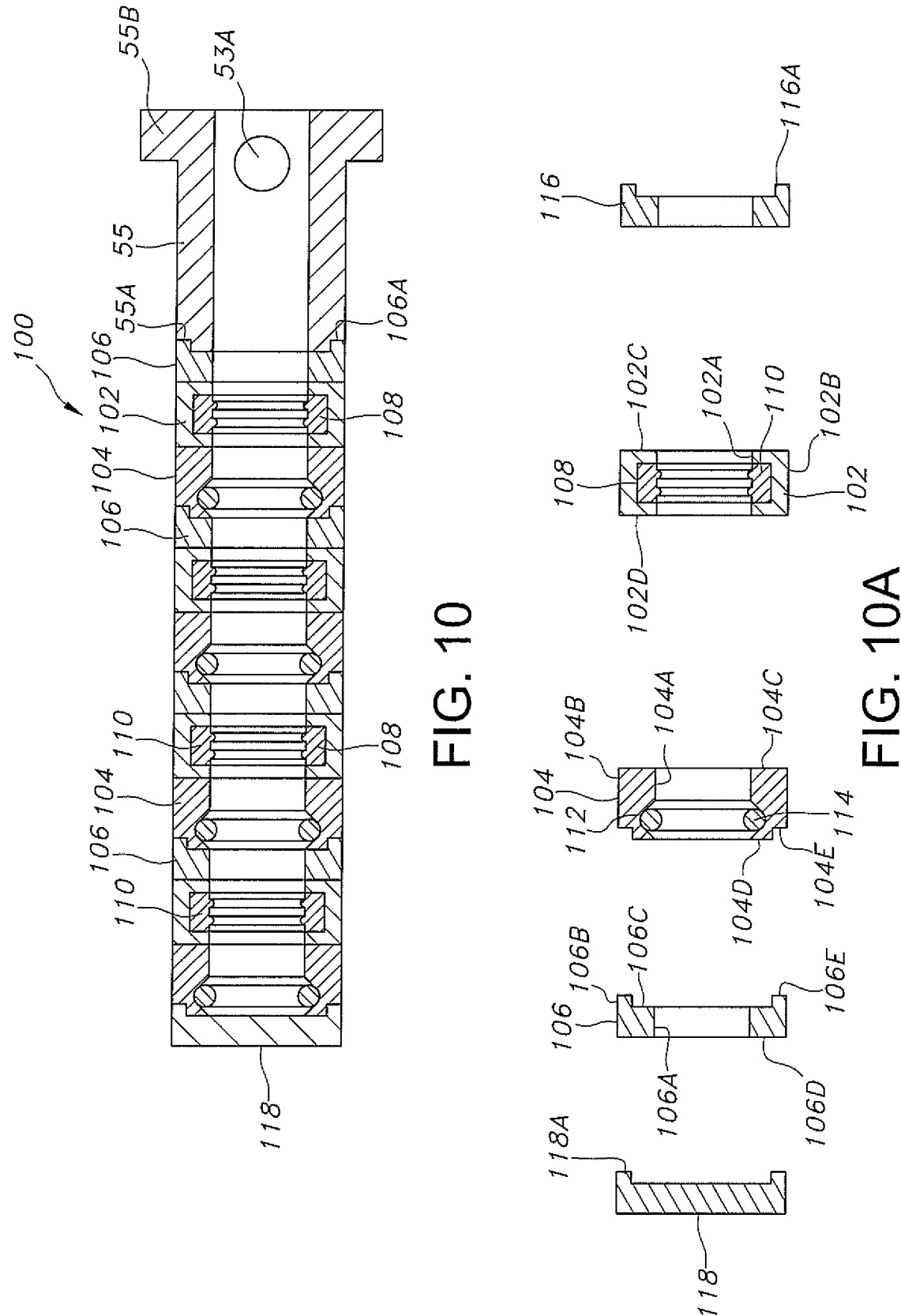
FIG. 10 is a cross-sectional view of another exemplary embodiment of the terminal housing assembly 100 shown in FIGS. 3 and 4.
FIG. 10A is a broken-apart view showing a polymeric insulator ring 102 housing a polymeric ring seal 68, a metallic terminal housing 104 that mates with a metallic fitting 106 for a metallic annular contact spring 114, and a terminal plate 118 for the terminal housing assembly 100 shown in FIG. 10.

FIGS. 10 and 10A illustrate another exemplary embodiment of a terminal housing assembly 100 according to the present invention. The terminal housing assembly 100 is comprised of alternating ceramic insulator rings 102 and ring-shaped metallic terminal contact assemblies, the latter being comprised of a ring-shaped metallic contact spring housing 104 that is mated to a ring-shaped metallic fitting 106.

The ceramic insulator rings 102 have an annularly-shaped, preferably cylindrically-shaped, inner wall 102A that is co-axially aligned with an annularly-shaped, preferably cylindrically-shaped, outer wall 102B. The inner and outer walls 102A, 102B extend to spaced-apart right and left planar sidewalls 102C and 102D. An inner annular groove 108 having a square- or rectangular-shape in cross-section resides in the inner wall 102A, centered between the right and left sidewalls 102C, 102D. A compliant polymeric ring seal 110 is seated in the inner annular groove 108. The polymeric ring seal 110 has a square- or rectangular-shaped base that seats in the inner annular groove 108 and an inwardly-extending pair of side-by-side annular protrusions that serve as side-by-side seals.

The ring-shaped metallic terminal housing 104 is one member of a terminal housing assembly. They have an annularly-shaped, preferably cylindrically-shaped, inner wall 104A that is co-axially aligned with an annularly-shaped, preferably cylindrically-shaped, outer wall 104B. The inner and outer walls 104A, 104B extend to spaced-apart right and left sidewalls 104C and 104D. The left sidewall 104D is provided with an inwardly-extending annular step 1042E at the outer wall 104B. An inner annular groove 112 having a semi-circular shape in cross-section resides in the inner wall 104A, off-centered towards the left sidewall 104D. A metallic annular contact spring 114 is seated in the annular groove 112. A suitable contact spring 114 is a BAL SEAL® type canted coil spring.

The ring-shaped metallic fitting 106 is the other member of a terminal housing assembly. The fittings 106 are each comprised of an annularly-shaped, preferably cylindrically-shaped, inner wall 106A that is co-axially aligned with an annularly-shaped, preferably cylindrically-shaped, outer wall 106B. The inner and outer walls 106A, 106B extend to spaced-apart right and left sidewalls 106C and 108D. The right sidewall 106C is provided with an outwardly-extending right annular rim 106E adjacent to the annularly-shaped outer wall 106B.

To construct the terminal housing assembly 100, the right and left sidewalls 102C and 102D of the ceramic insulator rings 102 are coated with a titanium metallization, preferably using a physical vapor deposition (PVD) process. Then, the left sidewall 106A of a metallic fitting 106 is contacted to the titanium coated right sidewall 102C of the ceramic insulator ring 102 and the titanium coated left sidewall 102D of the ceramic insulator ring 102 is contacted to the right sidewall 104C of a metallic terminal housing 104. This assembly is then subjected to an axial pressure aligned along the axis of the terminal housing assembly 100 ranging from about 1 MPa to about 5 MPa at a temperature ranging from about 850° C. to about 950° C. for up to about 2 hours. This serves to diffusion bond the PVD-deposited titanium metallization contacting the right sidewall 102C of a ceramic insulator ring 102 to the left sidewall 106D of a metallic fitting 106 and to diffusion bond the PVD-deposited titanium metallization contacting the left sidewall 102D of the ceramic insulator ring 102 to the right sidewall 104C of a metallic terminal housing 104 to thereby form a modular assembly.

A silicone ring seal 110 is seated in the inner annular groove 108 of the ceramic insulator ring 102 and a canted coil spring 114 is seated in the inner annular groove 112 of the terminal housing 104. The annular rim 106B of a metallic fitting 106 is then welded to the annular step 104E of the metallic terminal housing 104 to connect one modular assembly to an adjacent modular assembly to provide the terminal housing assembly 100 having the desired number of ceramic insulator rings 102 and terminal contact assemblies comprising a ring-shaped metallic terminal housing 104 connected to a metallic fitting 106. Preferably, there are from 2 to 24 insulator rings 102 connected to 2 to 24 terminal contact assemblies comprising a ring-shaped metallic terminal housing 104 connected to a metallic fitting 106 in an alternating configuration as described above.

A metallic terminal plate 118 has an outwardly-extending annular rim 118A. The annular rim 118A is welded to the annular step 104E of the distal-most metallic terminal housing 104. The annular step 55A of a proximal metallic sleeve 55 is welded to a proximal metallic fitting 106 diffusion bonded to the PVD-deposited titanium metallization contacted to the right sidewall 102C of the proximal-most ceramic insulator ring 102 to complete the terminal housing assembly 100. Laser or ultrasonically welding are preferred techniques for all of the welded connections.

In a similar manner as described above with respect to the terminal housing assembly 34 shown in FIGS. 6 and 7, the flange 55B of the proximal metallic sleeve 55 is welded to the inner surface of the end wall 32A of the end cap 32 with the main body of the terminal housing assembly 100 extending distally, out past the annular edge 36 of the end cap 32 and through the minor opening 38A in the cap plate 38. This aligns the longitudinal axis of the terminal housing assembly 100 at an orientation that is substantially perpendicular to the planar face of the cap plate 38 and substantially perpendicular to an imaginary plane aligned along the annular edge 36 of the end cap 32.

In use, the proximal end of a lead (not shown) is moved through the lead opening 54 (FIG. 5) in the curved end wall 32A of the end cap 32, through the metallic sleeve 55 and into the lumen provided by the terminal housing assembly 100 so that electrical contacts at the proximal end of the lead are aligned with and electrically connected to the canted coil springs 114 in the terminal housings 104. A fastener is threaded through the treaded opening 56 in the end cap 32 to intersect the lateral opening 53A in the sleeve 55 until the threaded fastener contacts the lead to secure the proximal end of the lead received in the terminal housing assembly 100 in place.

Even though body fluid can flow through the lead opening 54 and into the lumen of the terminal housing assembly 100, the fluid-impermeable connections between the sleeve 55, the alternating insulator rings 102 and terminal housings 104 and the terminal plate 118 prevent those fluid from seeping through the terminal housing assembly 100 and into the interior of the device housing 26. The ring seals 108 of the ceramic insulator rings 102 also help to electrically isolate adjacent terminal housings 104 from each other and they help to prevent ingress of body fluid into the interior of the AMD 12. In that respect, with the sleeve 51 welded to the inner surface of the end cap 32, body fluid could flow into the lumen of the terminal housing assembly 100, but the assembly 100 is impermeable to body fluid flowing through the connected insulator rings 102 and terminal housings 104/fittings 106 and into the interior of the device housing formed by the end cap 32 connected to the main housing 26.

Figures 11, 11A:
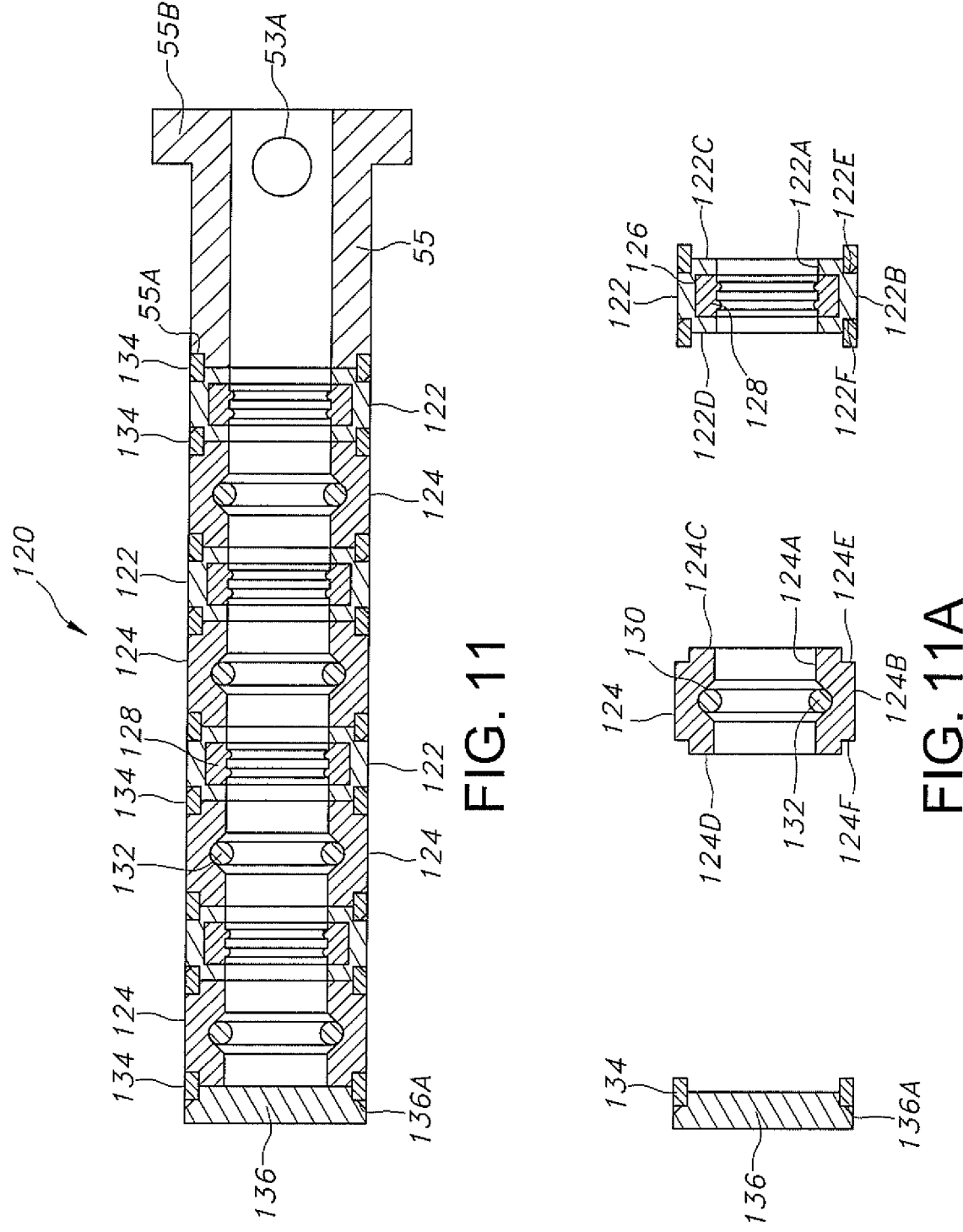
FIG. 11 is a cross-sectional view of another exemplary embodiment of the terminal housing assembly 120 shown in FIGS. 3 and 4.
FIG. 11A is a broken-apart view showing a polymeric insulator ring 122 housing a polymeric ring seal 128, a metallic terminal housing 124 for a metallic annular contact spring 132, and a terminal plate 136 for the terminal housing assembly 120 shown in FIG. 11.

FIGS. 11 and 11A illustrate another exemplary embodiment of a terminal housing assembly 120 according to the present invention. The terminal housing assembly 120 is comprised of alternating ceramic insulator rings 122 and ring-shaped metallic terminal housings 124. The ceramic insulator rings 122 have an annularly-shaped, preferably cylindrically-shaped, inner wall 122A that is co-axially aligned with an annularly-shaped, preferably cylindrically-shaped, outer wall 122B. The inner and outer walls 122A, 122B extend to spaced-apart right and left sidewalls 122C and 122D. The sidewalls 122C, 122D are provided with respective inwardly-extending right and left annular steps 122E and 122F adjacent to the annularly-shaped outer wall 122B. An inner annular groove 126 having a square- or rectangular-shape in cross-section resides in the inner wall 122A, centered between the right and left sidewalls 122C, 122D.

A compliant polymeric ring seal 128 is seated in the inner annular groove 126. The polymeric ring seal 128 has a square- or rectangular-shaped base that seats in the inner annular groove 126 and an inwardly-extending pair of side-by-side annular protrusions that serve as side-by-side seals. Alumina is a preferred material for the ceramic insulator rings 122 and silicone is a preferred material for the polymeric ring seal 128.

The ring-shaped metallic terminal housings 124 comprise an annularly-shaped, preferably cylindrically-shaped, inner wall 124A that is co-axially aligned with an annularly-shaped, preferably cylindrically-shaped, outer wall 124B. The inner and outer walls 124A, 124B extend to spaced-apart right and left sidewalls 124C and 124D. The sidewalls 124C, 124D are provided with respective inwardly-extending right and left annular steps 124E and 124F adjacent to the outer wall 124B. An inner annular groove 130 having a semi-circular shape in cross-section resides in the inner wall 124A, centered between the right and left sidewalls 124C, 124D. A metallic annular contact spring 132 is seated in the annular groove 130. A suitable contact spring 132 is a BAL SEAL® type canted coil spring. Titanium is a preferred material for the terminal housings 124.

To construct the terminal housing assembly 120, the left sidewall 122D of a first or proximal-most ceramic insulator ring 122 is contacted to the right sidewall 124C of a first or proximal-most metallic terminal housing 124. Then, the right sidewall 122C of a second ceramic insulator ring 122 is contacted to the left sidewall 122D of the first metallic terminal housing 124. This alternating sequence of a ceramic insulator ring 122/metallic terminal housing 124/ceramic insulator ring 122 continues until the terminal housing assembly 120 has the desired length. Preferably, there are from 2 to 24 insulator rings 122 connected to 2 to 24 terminal housings 124 in an alternating configuration as described above.

Then, a gold preform 134 is positioned in the annular channel formed by the abutting left annular step 122F of a ceramic insulator ring 122 and the right annular step 124E of a metallic terminal housing 124, and a gold preform is positioned in the annular channel formed by the abutting right annular step 122E of a ceramic insulator ring 122 and the left annular step 124F of a metallic terminal housing 124. A gold preform 134 is also positioned in the annular channel formed by the annular step 55A of the sleeve 55 and the right annular step 122E of the proximal-most ceramic insulator ring 122. Another gold preform 134 is positioned in an annular step 136A of a metallic terminal plate 136 contacted to the left sidewall 124D of the distal-most metallic terminal housing 124. This assembly is then subjected to a brazing operation to melt the various gold preforms so that when the gold cools and solidifies, the alternating ceramic insulator rings 122 and the metallic terminal housings 124 are fluid-impermeably connected together with the sleeve 55 being fluid-impermeably connected to the proximal-most ceramic insulator ring 122 and the terminal plate 136 being fluid-impermeably connected to the distal-most metallic terminal housing 124.

A polymeric ring seal 128 is then moved through the sleeve 55 and seated in each of the annular grooves 126 and an annular contact spring 132 is moved through the sleeve 55 and seated in each of the annular grooves 130.

In a similar manner as described above with respect to the terminal housing assembly 34 shown in FIGS. 6 and 7, the flange 55B of the proximal metallic sleeve 55 is welded to the inner surface of the end wall 32A of the end cap 32 with the main body of the terminal housing assembly 120 extending distally, out past the annular edge 36 of the end cap 32 and through the minor opening 38A in the cap plate 38. This aligns the longitudinal axis of the terminal housing assembly 120 at an orientation that is substantially perpendicular to the planar face of the cap plate 38 and substantially perpendicular to an imaginary plane aligned along the annular edge 36 of the end cap 32.

In use, the proximal end of a lead (not shown) is moved through the lead opening 54 (FIG. 5) in the curved end wall 32A of the end cap 32, through the metallic sleeve 55 and into the lumen provided by the terminal housing assembly 120 so that electrical contacts at the proximal end of the lead are aligned with and electrically connected to the canted coil springs 132 in the terminal housings 124. A fastener is then threaded through the treaded opening 56 in the end cap 32 to intersect the lateral opening 53A in the sleeve 55 until the threaded fastener contacts the lead to secure the proximal end of the lead received in the terminal housing assembly 120 in place. The ring seals 128 of the ceramic insulator rings 122 help prevent ingress of body fluid, and the like, through the end cap 32 to the metallic terminal housings 124 of the terminal housing assembly 120. In that respect, with the sleeve 51 welded to the inner surface of the end cap 32, body fluid could flow into the lumen of the terminal housing assembly 120, but the assembly 120 is impermeable to body fluid flowing through the connected insulator rings 122 and terminal housings 124 and into the interior of the device housing formed by the end cap 32 connected to the main housing 26.

Figures 12, 12A:
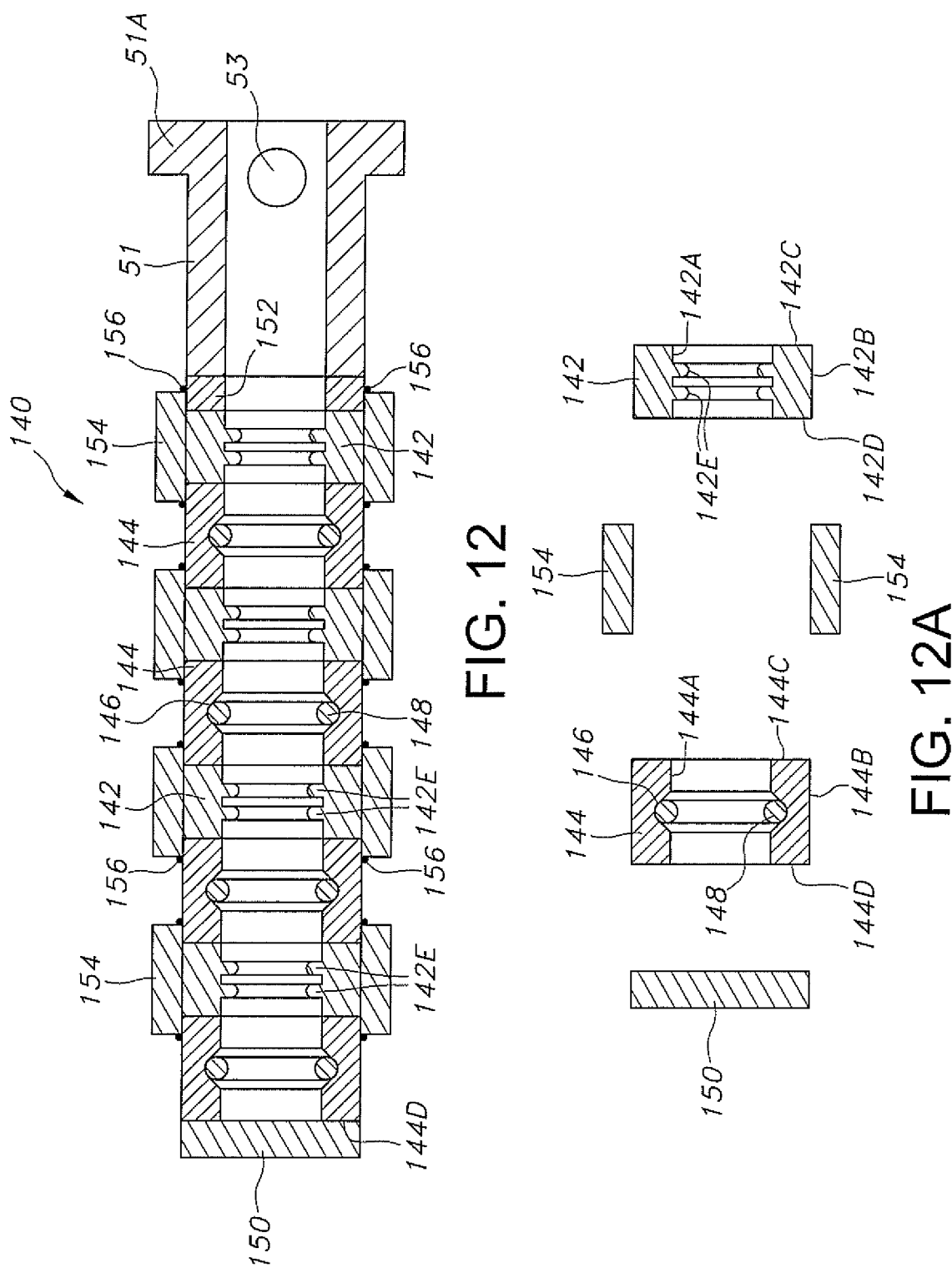
FIG. 12 is a cross-sectional view of another exemplary embodiment of the terminal housing assembly 140 shown in FIGS. 3 and 4.
FIG. 12A is a broken-apart view showing a polymeric ring seal 142, a metallic terminal housing 144 for a metallic annular contact spring 148, a terminal plate 150, and a sapphire ring 154 for welding the parts together to form the terminal housing assembly 140 shown in FIG. 12.

FIGS. 12 and 12A illustrate another exemplary embodiment of a terminal housing assembly 140 according to the present invention. The terminal housing assembly 140 is comprised of alternating compliant polymeric ring seals 142 and ring-shaped metallic terminal housings 144. The polymeric ring seals 142 have an annularly-shaped, preferably cylindrically-shaped, inner wall 142A that is co-axially aligned with an annularly-shaped, preferably cylindrically-shaped, outer wall 142B. The inner and outer walls 142A, 142B extend to spaced-apart right and left sidewalls 142C and 142D. A pair inwardly-extending side-by-side annular protrusions 142E serve as side-by-side seals. Silicone is a preferred material for the ring seal 142.

The ring-shaped metallic terminal housings 144 comprise an annularly-shaped, preferably cylindrically-shaped, inner wall 144A that is co-axially aligned with an annularly-shaped, preferably cylindrically-shaped, outer wall 144B. The inner and outer walls 144A, 144B extend to spaced-apart right and left sidewalls 144C and 144D. An inner annular groove 146 having a semi-circular shape in cross-section resides in the inner wall 144A, centered between the right and left sidewalls 144C, 144D. A metallic annular contact spring 148 is seated in the annular groove 146. A suitable contact spring 148 is a BAL SEAL® type canted coil spring. Titanium is a preferred material for the terminal housings 144.

To construct the terminal housing assembly 140, the left sidewall 142D of a first or proximal-most polymeric ring seal 142 is contacted to the right sidewall 144C of a first or proximal-most metallic terminal housing 144. Then, the right sidewall 142C of a second polymeric ring seal 142 is contacted to the left sidewall 144D of the first metallic terminal housing 144. This alternating sequence of a polymeric ring seal 142/metallic terminal housing 144/polymeric ring seal 142 continues until the terminal housing assembly 140 has the desired length. A metallic terminal plate 150 is contacted to the left sidewall 124D of the distal-most metallic terminal housing 124 and a proximal metallic ring 152 is contacted to the right sidewall 142C of the proximal-most polymeric ring seal 142. Preferably, there are from 2 to 24 insulator ring seals 82 connected to 2 to 24 terminal housings 144 in an alternating configuration as described above.

Then, a sapphire ring 154 is moved into contact with the outer annular sidewall 142B of each of the polymeric ring seals 142. The sapphire rings 150 are wide enough to bridge over the polymeric ring seals 142 and contact a portion of the outer annular surfaces 144B of the adjacent terminal housings 144. There is also a sapphire ring 154 that bridges over the proximal-most polymeric ring seal 142 to contact the proximal metallic ring 152 and the proximal-most terminal housing 144. Then, a laser beam (not shown) is directed at the sapphire ring 154 to form the hermetic seal at the junction where each of the sapphire rings 154 overlapping a polymeric ring seal 142 bridges to adjacent terminal housings 144 and overlapping the proximal-most ring seal 142 and bridges to the proximal-most terminal housing 144 and the proximal metallic ring 152. In that manner, various welds 156 are formed. Further, a proximal metallic sleeve 51 is welded to the right sidewall of the metallic ring 152 and a metallic terminal plate 150 is welded to the left sidewall 144D of the distal-most metallic terminal housing 144 to complete the terminal housing assembly 140.

In a similar manner as described above with respect to the terminal housing assembly 34 shown in FIGS. 6 and 7, the flange 51A of the proximal metallic sleeve 55 is welded to the inner surface of the end wall 32A of the end cap 32 with the main body of the terminal housing assembly 140 extending distally, out past the annular edge 36 of the end cap 32 and through the minor opening 38A in the cap plate 38. This aligns the longitudinal axis of the terminal housing assembly 140 at an orientation that is substantially perpendicular to the planar face of the cap plate 38 and substantially perpendicular to an imaginary plane aligned along the annular edge 36 of the end cap 32. The sleeve 51 also has a lateral opening 53 that aligns with the lateral treaded opening 56 in the end cap 32 (FIGS. 3 to 5). Laser or ultrasonically welding are preferred techniques for all of the welded connections.

In use, the proximal end of a lead (not shown) is moved through the lead opening 54 (FIG. 5) in the curved end wall 32A of the end cap 32, through the metallic sleeve 51 and into the lumen provided by the terminal housing assembly 140 so that electrical contacts at the proximal end of the lead are aligned with and electrically connected to the canted coil springs 148 in the terminal housings 144. A fastener is then threaded through the treaded opening 56 in the end cap 32 to intersect the lateral opening 53 in the sleeve 51 until the threaded fastener contacts the lead to secure the proximal end of the lead received in the terminal housing assembly 140 in place. The pair of inwardly-extending side-by-side annular protrusions 142E of the ring seals 142 help prevent ingress of body fluid, and the like, through the end cap 32 to the metallic terminal housings 144 of the terminal housing assembly 140. In that respect, with the sleeve 51 welded to the inner surface of the end cap 32, body fluid could flow into the lumen of the terminal housing assembly 140, but the assembly 140 is impermeable to body fluid flowing through the connected insulator rings 142, terminal housings 144, terminal plate 150, proximal fitting 152 and sleeve 51 and into the interior of the device housing formed by the end cap 32 connected to the main housing 26.

While titanium (e.g., grades 1, 5, 9, 23, and the like), is a preferred material for the terminal housings 42, 64, 84, 104/106, 124 and 144, the housings may be formed from any suitable metal or alloy or combination of metals or alloys that are biocompatible and suitable for implantation into a patient. In some examples, it may be desirable for the surface of a metallic terminal housing 42, 64, 84, 104/106, 124 and 144 to have a low surface roughness that wets well, e.g., to increase contact with reflowed material from a polymeric insulator ring 40, for example. In addition to titanium, suitable metal or alloys include at least one of stainless steel, tantalum, niobium, platinum, and iridium. In some examples, a metal or alloy may be selected that has desirable thermal behavior (e.g., in terms of conduction/absorption from a laser in a laser heating process). In some examples, the metallic terminal housings 42, 64, 84, 104/106, 124 and 144 may have surface modifications or other properties, e.g., surface roughness, cleanliness, oxides, in the area of their interface with polymeric insulator rings that promote better bonding with the polymer.

It is appreciated that various modifications to the inventive concepts described herein may be apparent to those skilled in the art without departing from the spirit and scope of the present invention as defined by the hereinafter appended claims.

What is claimed is:

1. An active medical device (AMD), comprising:
   a) a device housing, comprising:
      i) a main housing comprising a housing sidewall extending to a main housing annular edge surrounding a housing opening leading into an interior of the main housing; and
      ii) an end cap comprising an end cap sidewall extending to an end cap annular edge surrounding an end cap main opening leading into an interior of the end cap, the end cap annular edge aligned along an imaginary plane, wherein an end cap lead opening in the end cap sidewall is aligned with an end cap lead opening axis that extends through the interior of the end cap to intersect the imaginary plane, and an end cap lateral opening in the end cap sidewall is aligned with an end cap lateral opening axis that intersects the end cap lead opening axis, and wherein the end cap annular edge is connected to the main housing annular edge to close the device housing; and
   b) a printed circuit board (PCB) at least partially housed inside the device housing and supporting an x number of electrical contacts connected to a respective one of a y number of electronic components, wherein the x number of electrical contacts and the y number of electronic components are at least 3;
   c) an electrical power source housed inside the device housing to power the y number of electronic components;
   a) a metallic sleeve having a sleeve lumen extending along a sleeve axis from a sleeve proximal end having a sleeve proximal opening to a sleeve distal end having a sleeve distal opening, wherein the sleeve proximal end is connected to an inner surface of the end cap so that the sleeve proximal opening coincides with the end cap lead opening and so that the sleeve axis is aligned with the end cap lead opening axis, and wherein the sleeve has a sleeve lateral opening that intersects the sleeve lumen;

e) a terminal plate;

f) a terminal housing assembly having an m number of insulator rings connected to an n number of terminal housings in an alternating sequence extending distally from the sleeve distal end, the alternating sequence comprising a first of the m number of insulator rings connected to the sleeve distal end, a first of the n number of terminal housings connected to the first of the m number of insulator rings, a second of the m number of insulator rings connected to the first of the n number of terminal housings, a second of the n number of terminal housings connected to the second of the m number of insulator rings continuing distally to a distal-most one of the n number of terminal housings connected distally to a distal-most one of the m number of insulator rings, and the terminal plate is connected to the distal-most one of the n number of terminal housings opposite the distal-most one of the m number of insulator rings to thereby provide the terminal housing assembly extending distally outwardly beyond the imaginary plane at the end cap annular edge and having a central lumen the terminal housing assembly extending along a central axis aligned with the sleeve and the end cap lead opening axes, wherein the m number of insulator rings and the n number of terminal housings range from 3 to 24, and wherein the m number of insulator rings support respective polymeric ring seals, and the n number of terminal housings support respective metallic annular contact springs; and g) an o number of jumper wires directly connecting a respective one of the n number of terminal housings to a respective one of the x number of electrical contacts supported on the PCB.

2. The AMD of claim 1, wherein the polymeric ring seals are made of silicone.

3. The AMD of claim 1, wherein the metallic annular contact springs are canted coil springs.

4. The AMD of claim 1, wherein the o number of jumper wires directly connecting a respective one of the n number of terminal housings to a respective one of the x number of electrical contacts supported on the PCB reside in the main housing.

5. The AMD of claim 1, wherein a portion of the PCB that does not support the x number of electrical contacts extends into the interior of the end cap.

6. The AMD of claim 1, wherein the PCB has a PCB edge that extends along a PCB edge axis with the x number of electrical contacts being supported by the PCB at the PCB edge.

7. The AMD of claim 6, wherein the PCB edge axis is parallel to but spaced from the central axis of the central lumen extending through the terminal housing assembly.

8. The AMD of claim 1, a) wherein the m number of insulator rings are made of PEEK, and wherein the n number of terminal housings and the sleeve are made of titanium so that the terminal housing assembly has the alternating sequence extending distally from the sleeve distal end welded to a first of the m number of PEEK insulator rings welded to a first of the n number of titanium terminal housings welded to a second of the m number of PEEK insulator rings welded to a second of the n number of titanium terminal housings continuing distally to a distal-most one of the n number of titanium terminal housings connected distally to a distal-most one of the m number of PEEK insulator rings, wherein the m number of PEEK insulator rings and the n number of titanium terminal housings range from 3 to 24, and b) wherein the titanium terminal plate is welded to the distal-most one of the n number of titanium terminal housings opposite the distal-most one of the m number of PEEK insulator rings.

9. The AMD of claim 1, a) wherein the m number of insulator rings are made of alumina provided with a titanium metallization, and wherein the n number of terminal housings and the sleeve are made of titanium so that the terminal housing assembly has the alternating sequence extending distally from the sleeve distal end welded to a first of the m number of titanium metallized alumina insulator rings welded to a first of the n number of titanium terminal housings welded to a second of the m number of titanium metallized alumina insulator rings welded to a second of the n number of titanium terminal housings continuing distally to a distal-most one of the n number of titanium terminal housings connected distally to a distal-most one of the m number of titanium metallized alumina insulator rings, wherein the m number of titanium metallized alumina insulator rings and the n number of titanium terminal housings range from 3 to 24, and b) wherein the titanium terminal plate is welded to the distal-most one of the n number of titanium terminal housings opposite the distal-most one of the m number of titanium metallized alumina insulator rings.

10. The AMD of claim 1, further comprising:

a) the distal end of the sleeve having an inwardly-extending annular step, at least the first of the m number of insulator rings comprising an insulator ring outer annular sidewall meeting right and left inwardly-extending annular steps, and at least the first of the n number of terminal housings comprises a terminal housing outer annular sidewall meeting at least a right inwardly-extending annular step;

b) a first ring-shaped braze connecting the sleeve inwardly extending annular step to the right inwardly extending annular step of the first of the m number of insulator rings; and c) a second ring-shaped braze connecting the left inwardly extending annular step of the first of the m number of insulator rings to the right inwardly extending annular step of the first of the n number of terminal housings.

11. The AMD of claim 1, further comprising:

a) at least the first of the n number of terminal housings comprising a terminal housing outer annular sidewall meeting spaced-apart right and left sidewalls, b) wherein at least the first and second of the m number of insulator rings each comprise an insulator ring outer annular sidewall meeting spaced-apart right and left sidewalls, and wherein the left and right sidewalls of the respective first and second of the m number of insulator rings contact the respective right and left sidewalls of the first of the n number of terminal housings, and c) a sapphire ring contacting the outer annular sidewall of the first of the n number of terminal housings, wherein the sapphire ring is welded to the first and second outer annular sidewalls of the first and second of the m number of insulator rings but not to the outer annular sidewall of the first of the n number of terminal housings.

12. The AMD of claim 1, further comprising:

a) the first of the m number of insulator rings comprising an insulator ring outer annular sidewall meeting right and left inwardly-extending annular steps;

b) at least the first of the n number of terminal housings comprising an outwardly-extending right annular rim that is welded to the left annular step of the first of the m number of insulator rings; and c) a metallic ring-shaped spacer having an outwardly-extending left annular rim that is welded to the right annular step of the first of the m number of insulator rings, d) wherein a distal end of the sleeve is welded to the ring-shaped spacer opposite the first of the m number of insulator rings.

13. An active medical device (AMD) system, comprising:

a) an implantable lead extending from a lead proximal end having at least two spaced-apart first and second electrical contacts to a distal electrode that is configured for contact with body tissue;

b) active medical device (AMD), comprising:

i) a device housing, comprising:

A) a main housing comprising a housing sidewall extending to a main housing annular edge surrounding a housing opening leading into an interior of the main housing; and B) an end cap comprising an end cap sidewall extending to an end cap annular edge surrounding an end cap main opening leading into an interior of the end cap, the end cap annular edge aligned along an imaginary plane, wherein an end cap lead opening in the end cap sidewall is aligned with an end cap lead opening axis that extends through the interior of the end cap to intersect the imaginary plane, and an end cap lateral opening in the end cap sidewall is aligned with an end cap lateral opening axis that intersects the end cap lead opening axis, and wherein the end cap annular edge is connected to the main housing annular edge to close the device housing; and ii) a printed circuit board (PCB) at least partially housed inside the device housing and supporting an x number of electrical contacts connected to a respective one of a y number of electronic components, wherein the x number of electrical contacts and the y number of electronic components are at least 2;

iii) an electrical power source housed inside the device housing to power the y number of electronic components;

iv) a metallic sleeve having a sleeve lumen extending along a sleeve axis from a sleeve proximal end having a sleeve proximal opening to a sleeve distal end having a sleeve distal opening, wherein the sleeve proximal end is connected to an inner surface of the end cap so that the sleeve proximal opening coincides with the end cap lead opening and so that the sleeve axis is aligned with the end cap lead opening axis, and wherein the sleeve has a sleeve lateral opening that intersects the sleeve lumen;

v) a terminal plate;

vi) a terminal housing assembly having an m number of insulator rings connected to an n number of terminal housings in an alternating sequence extending distally from the sleeve distal end, the alternating sequence comprising a first of the m number of insulator rings connected to the sleeve distal end, a first of the n number of terminal housings connected to the first of the m number of insulator rings, a second of the m number of insulator rings connected to the first of the n number of terminal housings, a second of the n number of terminal housings connected to the second of the m number of insulator rings continuing distally to a distal-most one of the n number of terminal housings connected distally to a distal-most one of the m number of insulator rings, and the terminal plate is connected to the distal-most one of the n number of terminal housings opposite the distal-most one of the m number of insulator rings to thereby provide the terminal housing assembly extending distally outwardly beyond the imaginary plane at the end cap annular edge and having a central lumen of the terminal housing assembly extending along a central axis aligned with the sleeve and the end cap lead opening axes, wherein the m number of insulator rings and the n number of terminal housings range from 3 to 24, and wherein the m number of insulator rings support respective polymeric ring seals, and the n number of terminal housings support respective metallic canted coil springs; and vii) an o number of jumper wires directly connecting a respective one of the n number of terminal housings to a respective one of the x number of electrical contacts supported on the PCB, c) wherein the end cap lead opening in the end cap sidewall is configured to receive the proximal end of the lead moved into the central lumen of the terminal housing assembly so that when the first and second lead contacts at the lead proximal end are in electrical continuity with the canted coil springs of the respective first, second and the distal-most one of the n number of terminal housings, electrical continuity is established from the distal electrode of the lead to the canted coil springs of respective ones of the n number of terminal housings and to respective ones of the o number of jumper wires connected to respective ones of the x number of electrical contacts connected to respective ones of the y number of electronic components supported on the PCB, and d) wherein the lead is configured to at least one of deliver electrical stimulation to body tissue or sense biological signals from body tissue.

14. An active medical device (AMD), comprising:

a) a device housing, comprising:

i) a main housing comprising a housing sidewall extending to a main housing annular edge surrounding a housing opening leading into an interior of the main housing; and ii) an end cap comprising an end cap sidewall extending to an end cap annular edge surrounding an end cap main opening leading into an interior of the end cap, the end cap annular edge aligned along an imaginary plane, wherein an end cap lead opening in the end cap sidewall is aligned with an end cap lead opening axis that extends through the interior of the end cap to intersect the imaginary plane, and an end cap lateral opening in the end cap sidewall is aligned with an end cap lateral opening axis that intersects the end cap lead opening axis, and wherein the end cap annular edge is connected to the main housing annular edge to close the device housing; and b) a printed circuit board (PCB) at least partially housed inside the device housing and supporting at least a first and a first+x number of electrical contacts connected to respective ones of a first and a first+y number of electronic components, wherein the first and the first+x number of electrical contacts and the first and the first+y number of electronic components are at least 2;

c) an electrical power source housed inside the device housing to power at least the first and the first+y number of electronic components;

d) a metallic sleeve having a sleeve lumen extending along a sleeve axis from a sleeve proximal end having a sleeve proximal opening to a sleeve distal end having a sleeve distal opening, wherein the sleeve proximal end is connected to an inner surface of the end cap so that the sleeve proximal opening coincides with the end cap lead opening and so that the sleeve axis is aligned with the lead opening axis, and wherein the sleeve has a sleeve lateral opening that intersects the sleeve lumen;

e) a terminal plate;

f) a terminal housing assembly having an m number of insulator rings connected to an n number of terminal housings in an alternating sequence extending distally from the sleeve distal end, wherein the alternating sequence comprises a first of the m number of insulator rings connected to the sleeve distal end, a first of the n number of terminal housings connected to the first of the m number of insulator rings, a first+1 of the m number of insulator rings connected to the first of the n number of terminal housings, a first+1 of the n number of terminal housings connected to the first+1 of the m number of insulator rings, a first+2 of the n number of terminal housings connected to the first+1 of the m number of insulator rings continuing distally to a distal-most one of the n number of terminal housings connected to a distal-most one of the m number of insulator rings, and wherein the terminal plate is connected to the distal-most one of the n number of terminal housings opposite the distal-most one of the m number of insulator rings to thereby provide the terminal housing assembly extending distally outwardly beyond the imaginary plane at the end cap annular edge and having a central lumen of the terminal housing assembly extending along a central axis aligned with the sleeve and the end cap lead opening axes, wherein the m number of insulator rings and the n number of terminal housings range from 4 to 24, and wherein the m number of insulator rings support respective polymeric ring seals, and the n number of terminal housings support respective metallic annular contact springs; and g) an o number of jumper wires directly connecting a respective one of the n number of terminal housings to a respective one of the x number of electrical contacts supported on the PCB.

15. The AMD of claim 14, wherein, if the m number of insulator rings and the n number of terminal housings are greater than 4, the first+m number of insulator rings connected to the first+n number of terminal housings is a repeating sequence with m and n being the same and >4.

16. The AMD of claim 14, wherein the PCB has a PCB edge that extends along a PCB edge axis with the first and the first+x number of electrical contacts being supported by the PCB at the PCB edge.

17. The AMD of claim 14, a) wherein the m number of insulator rings are made of PEEK, and wherein the n number of terminal housing and the sleeve are made of titanium so that the terminal housing assembly has the configuration extending distally from the sleeve of: the distal end of the titanium sleeve welded to the first PEEK insulator ring welded to the first titanium terminal housing welded to the first+1 PEEK insulator ring welded to the first+1 titanium terminal housing, and b) wherein, if the m number of insulator rings and the n number of terminal housings are greater than 4, the first+m PEEK insulator rings connected to the first+n titanium terminal housings is a repeating sequence with m and n being the same and >4, and c) wherein the terminal plate is connected to the distal-most titanium terminal housing.

18. The AMD of claim 1, a) wherein the first and the first+m number of insulator rings are made of alumina provided with a titanium metallization, and wherein the first and the first+n number of terminal housings and the sleeve are made of titanium so that the terminal housing assembly has the configuration extending distally from the sleeve of: the titanium sleeve welded to the first titanium metallized alumina insulator ring welded to the first titanium terminal housing welded to the first+1 titanium metallized alumina insulator ring welded to the first+1 titanium terminal housing, and b) wherein, if the m number of insulator rings and the n number of terminal housings are greater than 1, the first+m titanium metallized alumina insulator ring welded to the first+n titanium terminal housing is a repeating sequence with m and n being the same and >4, and c) wherein the terminal plate is connected to the distal-most titanium terminal housing.

19. The AMD of claim 14, wherein the x number of electrical contacts and the o number of jumper wires are the same as the m number of insulator rings and the n number of terminal housings ranging from 4 to 24.

20. The AMD of claim 1, wherein the x number of electrical contacts and the o number of jumper wires are the same as the m number of insulator rings and the n number of terminal housings ranging from 3 to 24.

21. The AMD of claim 1, wherein the end cap lead opening axis extending through the interior of the end cap intersect the imaginary plane at a right angle.

22. The AMD of claim 1, wherein the end cap lateral opening is treaded, and wherein the sleeve lateral opening is aligned with the threaded end cap lateral opening.

23. The AMD of claim 1, wherein the m number of insulator rings and the n number of terminal housings are the same.

* * * * *